(12) United States Patent
Varadan

(10) Patent No.: US 11,399,769 B2
(45) Date of Patent: *Aug. 2, 2022

(54) SMART MATERIALS, DRY TEXTILE SENSORS, AND ELECTRONICS INTEGRATION IN CLOTHING, BED SHEETS, AND PILLOW CASES FOR NEUROLOGICAL, CARDIAC AND/OR PULMONARY MONITORING

(71) Applicant: NANOWEAR INC., Brooklyn, NY (US)

(72) Inventor: Vijay Varadan, State College, PA (US)

(73) Assignee: NANOWEAR INC., Brooklyn, NY (US)

( * ) Notice: Subject to any disclaimer, the term of this patent is extended or adjusted under 35 U.S.C. 154(b) by 14 days.

This patent is subject to a terminal disclaimer.

(21) Appl. No.: 16/914,312

(22) Filed: Jun. 27, 2020

(65) Prior Publication Data

US 2020/0390394 A1 Dec. 17, 2020

Related U.S. Application Data

(60) Division of application No. 15/668,036, filed on Aug. 30, 2017, now Pat. No. 10,932,720, which is a (Continued)

(51) Int. Cl.
*A61B 5/00* (2006.01)
*A61B 5/25* (2021.01)
*A61B 5/282* (2021.01)

(52) U.S. Cl.
CPC .............. *A61B 5/6804* (2013.01); *A61B 5/25* (2021.01); *A61B 5/282* (2021.01); *A61B 2562/0215* (2017.08)

(58) Field of Classification Search
CPC . A61B 5/0006; A61B 5/0402; A61B 5/04028; A61B 5/0452–0472;
(Continued)

(56) References Cited

U.S. PATENT DOCUMENTS 4,367,752 A 1/1983 Jimenez et al.
5,501,229 A 3/1996 Sekler et al.
(Continued)

OTHER PUBLICATIONS

Lao et al. "Hierarchical Oxide Nanostructures" J. Mater. Chem., 14, 770-773. Oct. 23, 2003.
(Continued)

*Primary Examiner* — Nathan J Jenness
(74) *Attorney, Agent, or Firm* — Davidson, Davidson & Kappel, LLC

(57) ABSTRACT

Sensors mounted on a textile include at least one of electrically conductive textile electrodes; single or multiple optically coupled infrared and red emitter and photodiode or photo transistor; and thin film or Resistive Temperature Detector (RTD). Textile electrodes, electrical connections, and electrical functionalization use at least one of nanoparticles, nanostructures, and mesostructures. Conductive thread, for electrical connections, may include a fiber core made from conductive materials such as but not limited to metals, alloys, and graphine structures, and a sheath of insulating materials such as but not limited to nylon, polyester, and cotton.

23 Claims, 30 Drawing Sheets

Related U.S. Application Data continuation-in-part of application No. 13/829,898, filed on Mar. 14, 2013, now abandoned, and a continuation-in-part of application No. 13/657,854, filed on Oct. 22, 2012, now abandoned, said application No. 13/829,898 is a continuation-in-part of application No. 13/449,755, filed on Apr. 18, 2012, now abandoned, said application No. 13/657,854 is a continuation of application No. 13/415,698, filed on Mar. 8, 2012, now abandoned.

(60) Provisional application No. 61/450,423, filed on Mar. 8, 2011.

(58) Field of Classification Search
CPC ... A61B 5/6804; A61B 5/6805; A61B 5/6823; A61B 2562/0285; G06F 19/3418; G08B 21/0211; G08B 21/0453
See application file for complete search history.

(56) References Cited

U.S. PATENT DOCUMENTS

| | | | |
|---|---|---|---|
| 5,749,365 | A | 5/1998 | Magill |
| 5,802,607 | A | 9/1998 | Triplette |
| 5,853,005 | A | 12/1998 | Scanlon |
| 6,047,203 | A | 4/2000 | Sackner et al. |
| 6,662,032 | B1 | 12/2003 | Gavish et al. |
| 6,687,523 | B1 | 2/2004 | Jayaramen et al. |
| 7,136,693 | B2 | 11/2006 | Brodnick |
| 7,319,895 | B2 | 1/2008 | Klefstad-Sillonville et al. |
| 7,354,877 | B2 | 4/2008 | Rosenberger et al. |
| 7,390,760 | B1 | 7/2008 | Chen et al. |
| 7,559,902 | B2 | 7/2009 | Ting et al. |
| 7,592,276 | B2 | 9/2009 | Hill |
| 7,857,777 | B2 | 12/2010 | Larson et al. |
| 7,862,624 | B2 | 1/2011 | Tran |
| 7,871,700 | B2 | 1/2011 | Poulin et al. |
| 8,348,841 | B2 | 1/2013 | Varadan |
| 10,932,720 | B2 * | 3/2021 | Varadan .................. A61B 5/25 |
| 2005/0034485 | A1 | 2/2005 | Klefstad-Sillonville et al. |
| 2006/0024499 | A1 | 2/2006 | Kim et al. |
| 2006/0175581 | A1 | 8/2006 | Douglas et al. |
| 2006/0252999 | A1 | 11/2006 | Devaul et al. |
| 2006/0282021 | A1 | 12/2006 | Devaul et al. |
| 2007/0049842 | A1 | 3/2007 | Hill et al. |
| 2007/0120297 | A1 | 5/2007 | Weider |
| 2008/0083740 | A1 | 4/2008 | Kaiserman et al. |
| 2008/0139911 | A1 | 6/2008 | Chandrasekaran et al. |
| 2008/0287769 | A1 | 11/2008 | Kurzweil et al. |
| 2009/0024017 | A1 | 1/2009 | Ruffini et al. |
| 2009/0088652 | A1 | 4/2009 | Tremblay |
| 2009/0306485 | A1 | 12/2009 | Bell |
| 2010/0185398 | A1 | 7/2010 | Berns et al. |
| 2010/0198038 | A1 | 8/2010 | Nagata et al. |
| 2010/0273049 | A1 | 10/2010 | Vidal et al. |
| 2010/0274100 | A1 | 10/2010 | Bahar et al. |
| 2011/0004088 | A1 | 1/2011 | Grossman |
| 2011/0260115 | A1 | 10/2011 | Kim |
| 2013/0281795 | A1 | 10/2013 | Varadan |
| 2013/0281815 | A1 | 10/2013 | Varadan |
| 2016/0222539 | A1 | 8/2016 | Varadan et al. |
| 2017/0225447 | A1 | 8/2017 | Varadan et al. |
| 2017/0226643 | A1 | 8/2017 | Varadan et al. |

OTHER PUBLICATIONS

Uberoi, et al., Interpretation of the Electrocardiogram of Young Athletes, Circulation, 124: 746-757 (2011).

American Heart Association, "Heart Rate Variability: Standards of Measurement, Physiological Interpretation, and Clinical Use" Circulation. 1996; 93: 1043-1065.

Dekker et al., "Heart Rate Variability from Short Electrocardiographic Recordings predicts Mortality from All Causes in Middle-Aged and Elderly Men" American Journal of Epidemiology, vol. 145, No. 10, 1997, 899-908, http:aje.oxfordjournals.org/accessed on Oct. 25, 2012.

Huei et al., "Develop an efficient Electrode to detect ECG signal" download from the internet prior to Aug. 19, 2011.

Hulley et al., "Randomized Trial of Estrogen Plus Progestin for Secondary Prevention of Coronary Heart Disease in Postmenopausal Women" Estrogen Plus Progestin and CHD, JAMA Aug. 19, 1998—vol. 280, No. 7 (9 pages).

Indiareport, "Now a vest that tracks medical condition" dated Oct. 12, 2011, http://www.indiareport.com/news-details/print_news.php?id=11 . . . accessed Oct. 13, 2011 (1 page).

Jahrsdoerfer et al., "Clinical Usefulness of the EASI 12-Lead Continuous Electrocardiographic Monitoring System" CritCare Nurse 2005; 25:28-37, cnn.aacnjournals.org, accessed on Oct. 25, 2012.

Kleber, "ST-segment elevation in the electrocardiogram: a sign of myocardialischemia" Cardiovascular Research 45 (2000)111-118.

Leicht et al., "Heart rate variability and endogenous sex hormones during the menstrual cycle in young women" Experimental Physiology, Manuscript received Nov. 28, 2002, ep.physoc.org, accessed Oct. 25, 2012 (6 pages).

Leonarduzzi et al., "Wavelet Leader Based Multifractal Analysis of heart Rate Variability during Myocardial Ischemia" 32nd Annual International Conference of the IEEE Embs Buenos Aires, Argentina, Aug. 31-Sep. 4, 2010 (4 pages).

Llyod-Jones et al., "Heart Disease and Stroke Statistics—2010 Update, a Report from the American Heart Association" Circulation, http//circ.ahajournals.org/accessed on Oct. 25, 2012.

Narayan., "T-Wave Alternans and the Susceptibility to Ventricular Arrhythmias" Journal of the American College of Cardiology , vol. 47, No. 2, 2006, 269-281.

Nussmeier "The female perspective: Gender in cardiothoracic surgery" The Journal of Thoracic and Cardiovascular Surgery, Sep. 2003, 126: 618-9.

Pan et al., "A Real-Time QRS Detection Algorithm" IEEE Transactions on Biomedical Engineering, 328.

Rudinac et al., "Fractal and Multifractal Analysis of heart Rate Variability" Telsiks, Sep. 26-28, 2007, 325-328.

Scanlon, "Acoustic Sensor Pad for Physiology Monitoring" Proceedings—19th International Conference—IEEE/EMBS Oct. 30-Nov. 2, 1997 (4 pages).

Tabibiazar et al., "Silent Ischemia in People with Diabetes: A Condition That Must Be Heard" Clincal Diabetes, vol. 21, No. 1, 2003 (5pages).

Varadan et al. "e-bra with Nanosensors for Real Time Cardiac Health Monitoring and Smartphone Communication" journal of Nanotechnology in Engineering and Medicine, May 1, 2011, vol. 2 (7 pages).

Varadan et al. "e-Nanoflex Sensor System: Smartphone-Based Roaming Health Monitor" Journal of Nanotechnology in Engineering and Medicine Feb. 1, 2010, vol. 2 (11 pages).

Varadan, "Wireless Point-of-Care Diagnosis for Sleep Disorder With Dry Nanowire Electrodes" Journal of Nanotechnology in Engineering and Medicine Aug. 2010, vol. 1 (11 pages).

Varadan, "Am EKG in your Underwear. Nanostructured sensors, smartphones, and cloud computing promise a new platform everyday medical morning." Mechanical Engineering Magazine, http://memagazine.asme.org/Articles/2011/October/EKG_Underwear.cfm? PrintPage=yes, accessed Oct. 14, 2011 (5pages).

Zhang et al. "Pulse Transit—Time based Blood pressure Estimation Using Hilbert-Huang Transform" 31st Annual International Conference of the IEEE EMBS Minneapolis, Minnesota, USA, Sep. 2-6, 2009 (4pages).

Vijay K. Varadan; Prashanth S. Kumar; Sechang Oh; Gyanesh N. Mathur; Pratyush Rai; Lauren Kegley; E-bra with nanosensors, smart electronics and smart phone communication network for heart rate monitoring. Proc. SPIE 7980, Nanosensors, Biosensors, and Info-Tech Sensorsand Systems 2011, 79800S (Apr. 13, 2011); doi:10.1117/12.885649.

Growth of highly oriented carbon nanotubes by plasma-enhanced hot filament chemical vapor deposition Huang, Z. P. and Xu, J. W.

(56) References Cited

OTHER PUBLICATIONS and Ren, Z.F. and Wang, J. H. and Seigal, M. P. and Provencio, P. N., Applied Physics Letters, 73, 3845-3847 (1998), DOI:http://dx.doi.org/10.1063/1. 122912.

Bordjiba, Mohamed Mohamedi1 and Le H Dao. Binderless carbon nanotube/carbon fibre composites for electrochemical micropower sources, nanotechnology, vol. 18, No. 3 Published Jan. 3, 2007.

Kong et al., "Spontaneous Polarization—Induced Nanohelixes, Nanosprings, and Nanorings of Peizoelectric Nanobelts" Nano Lett. vol. 3, 12 1625-1631 (2003).

Zhou, Zhengping and Wu, Xiang-Fa and Fong, Hao. Electrospun carbon nanofibers surface-grafted with vapor-grown carbon nanotubes as hierarchical electrodes for supercapacitors, Applied Physics Letters, 100, 023115 (2012).

Yan et al. (Helical Polyaniline Nanofibers Induced by Chiral Dopants by a Polymerization Process. Advanced Mateirals. 2007, 19, 3353-3357).

Kim et al. (Fabrication of carbon nanofiber, Cu Composite powder by electroless plating and microstructural evolution during thermal exposure, Scripta Materialia, vol. 52, Issue 10, May 2005, pp. 1045-1049).

Park et al. (Growth and high current field emission of carbon nanofiber films with electroplated Ni catalyst, Diamond and Related Materials, vol. 14, issues 11-12, Nov.-Dec. 2005, pp. 2094-2098).

McGary et al. (Magnetic nanowires for acoustic sensors, J. Appl. Phys. 99, 088310 (2006).

Rai, Pratyush, "Hybrid Nanostructured Textile Bioelectrode for Unobtrusive Health Monitoring" (Aug. 2013). Theses and Dissertations. 893 (Year: 2013).

\* cited by examiner

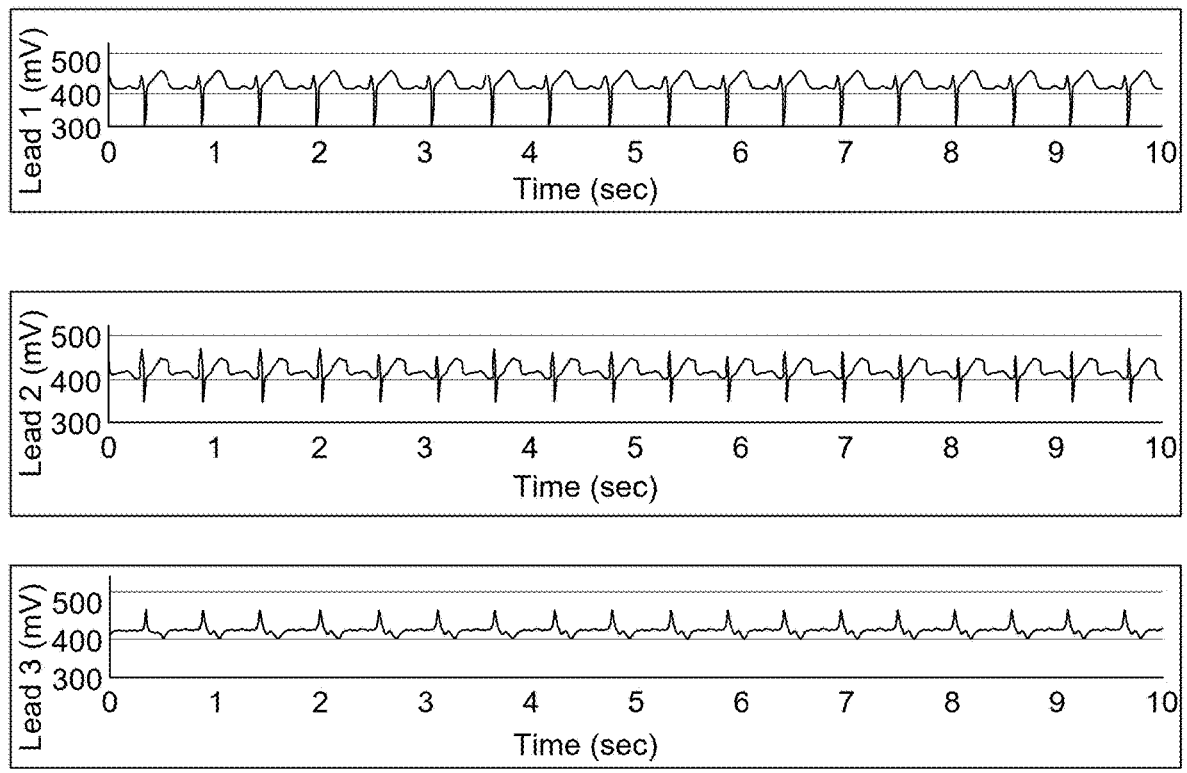
Figure 4: Signal from the 3 Lead ECG dry textile electrodes system- Lead 1, 2, and 3- plotted simultaneously.

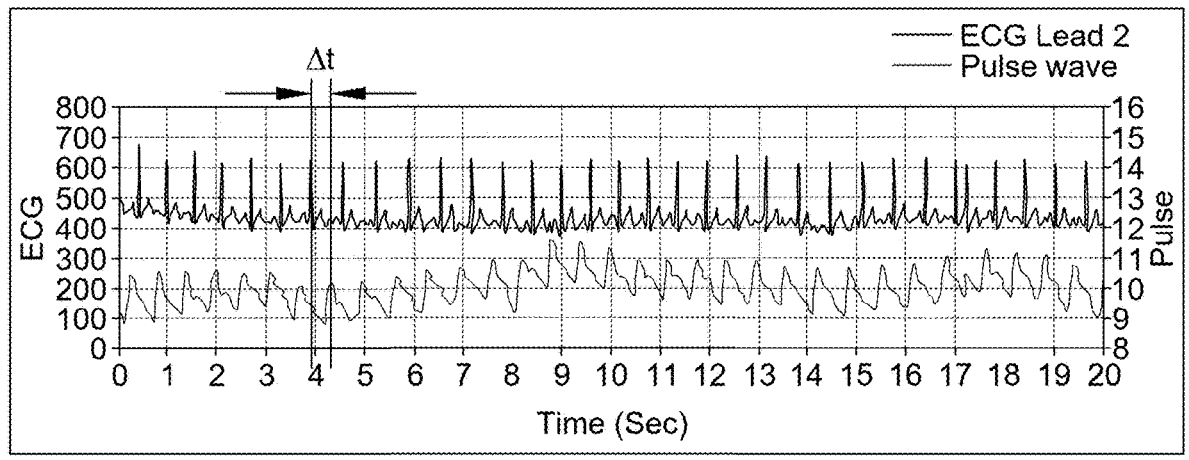
Figure 5: Leading Electrocardiograph (lead 2) and lagging brachial artery pulse data acquired on the same time line for measurement of pulse transit time ($\Delta t$)
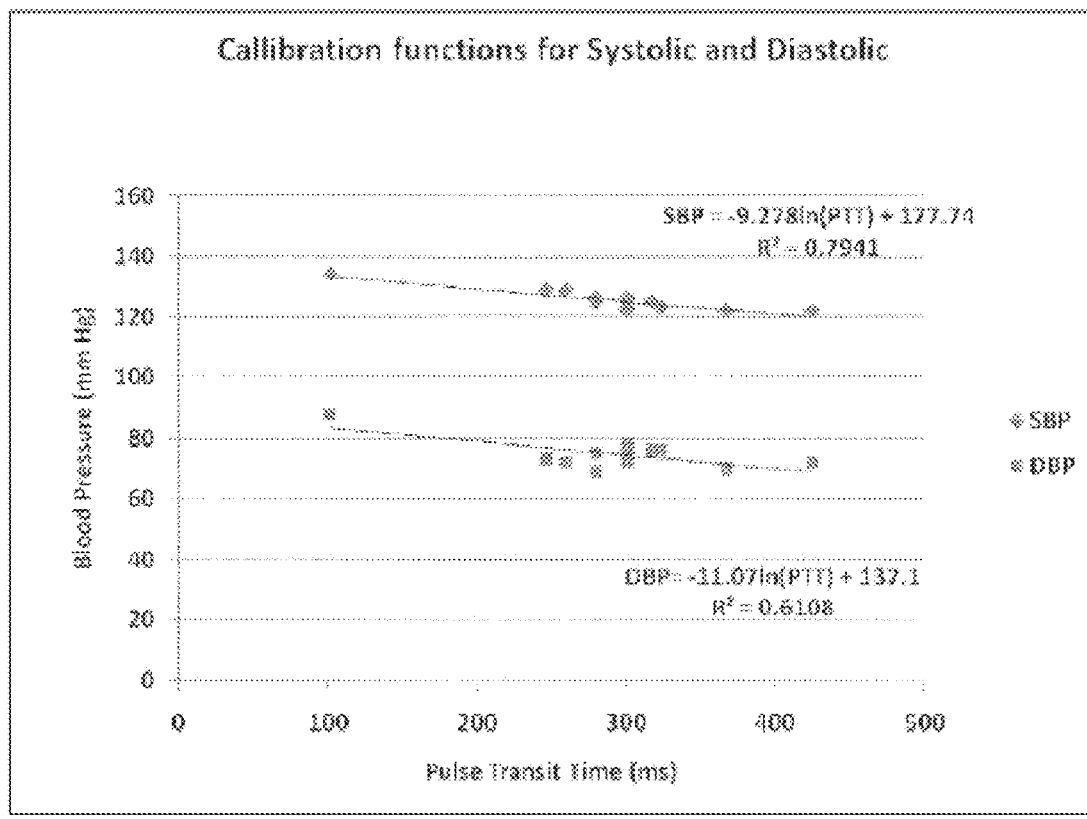
Figure. 6: Calibration curves for systolic and diastolic blood pressures versus pulse transit time.

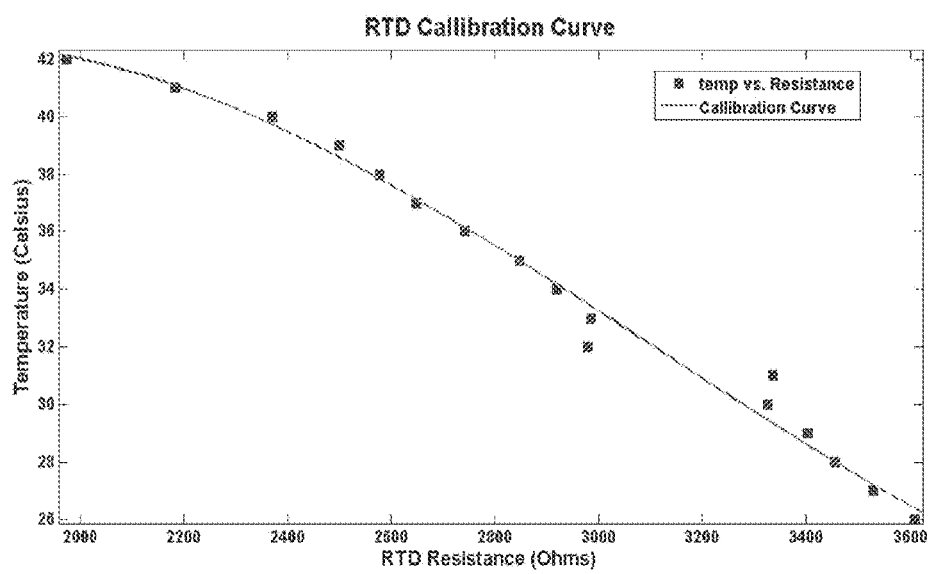
Figure 7: Resistive Temperature Detector based temperature sensor calibration curve: Temperature (°C) vs. Resistance (Ω)

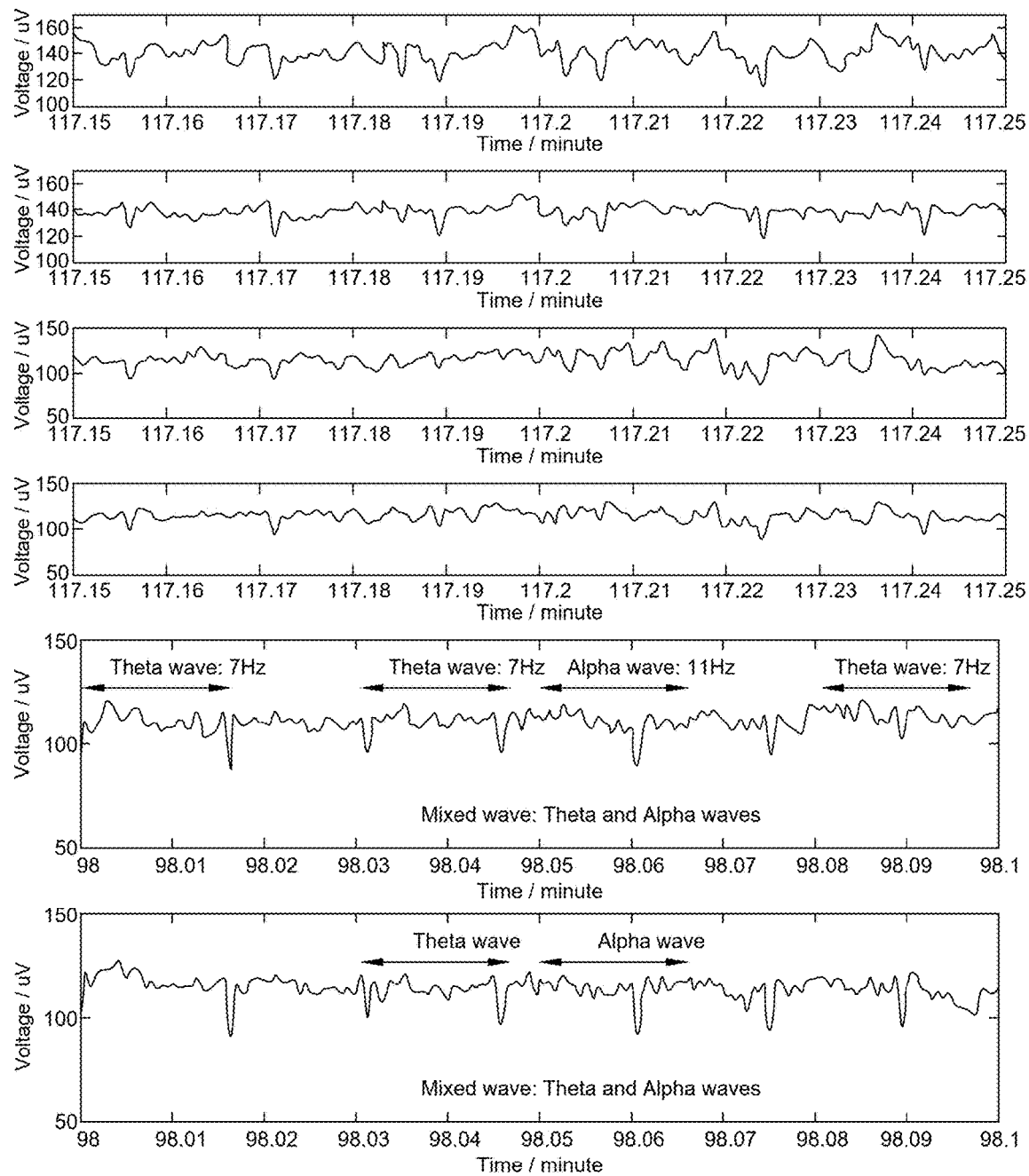
Figure 8: Textile sensor in pillow cases and bed sheets for brain rhythm such as Alpha, Beta, Theta and Delta waves

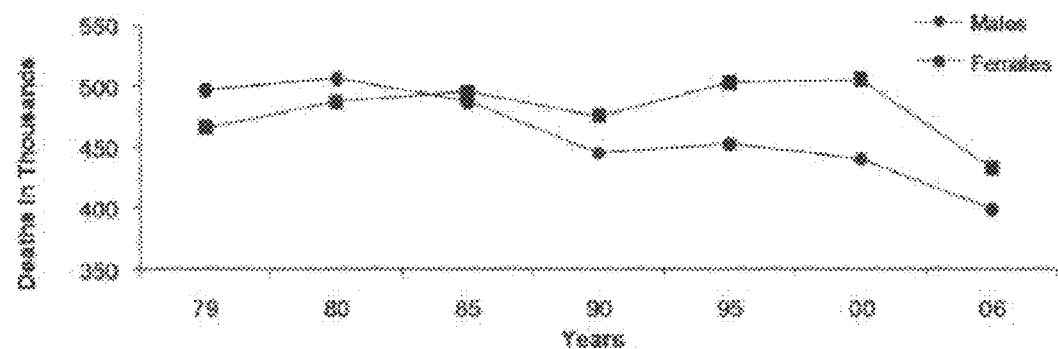
Figure 16
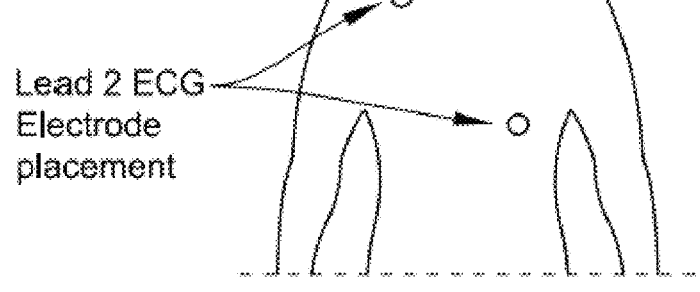
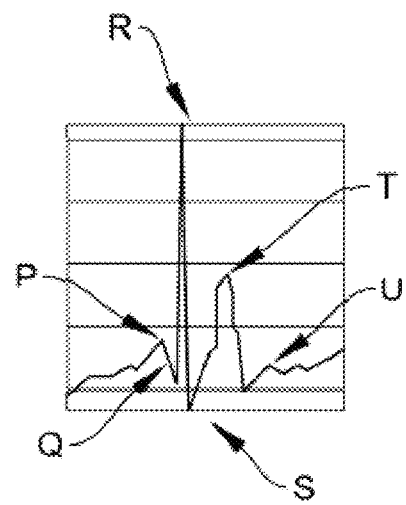
Figure 17A
Figure 17B

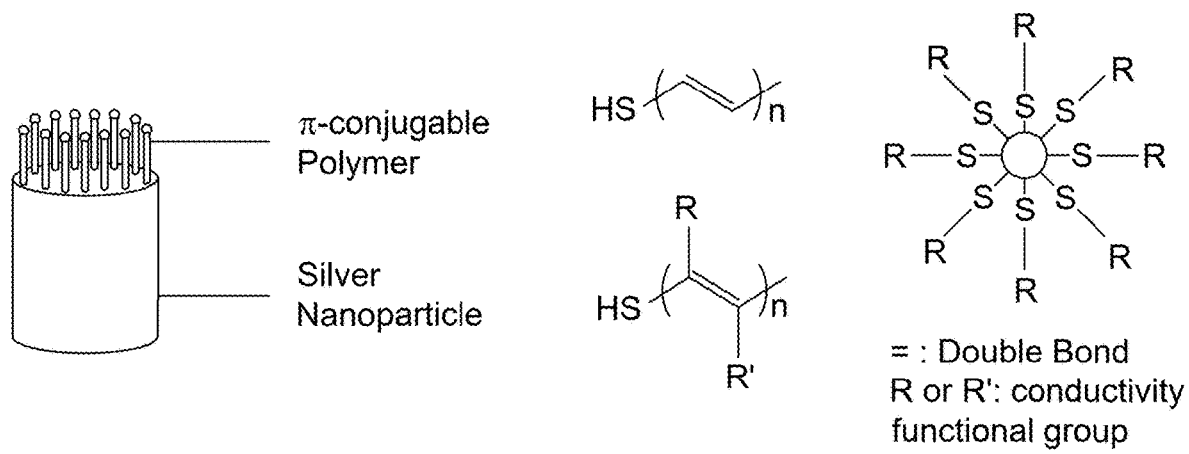
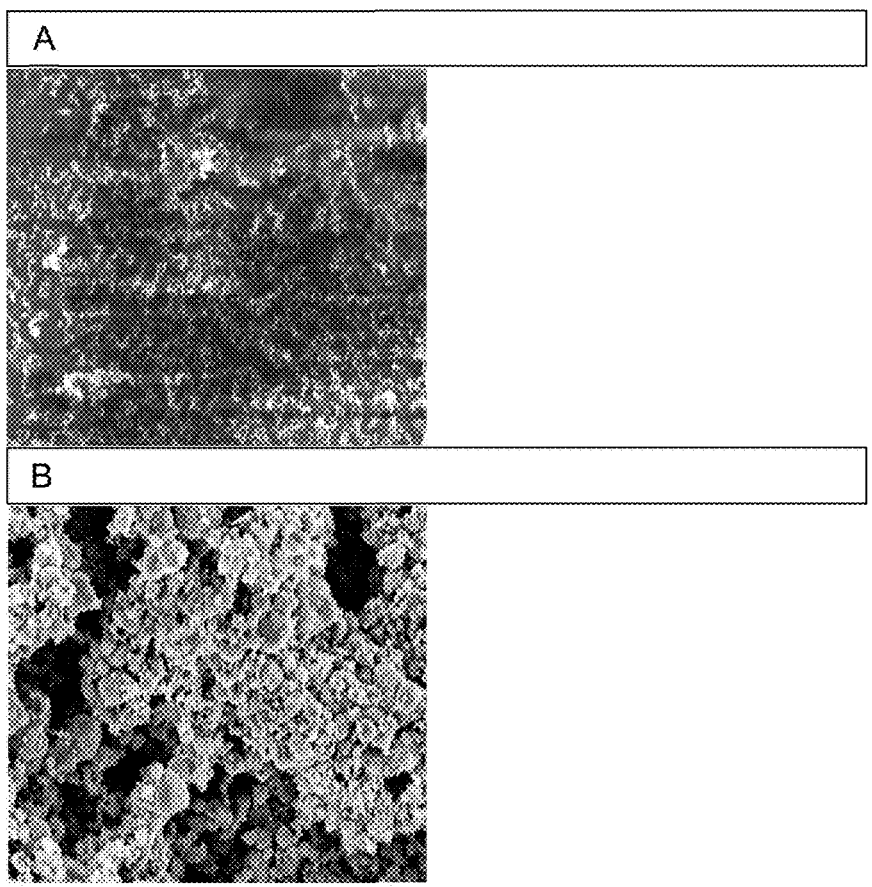
Figure 31

SMART MATERIALS, DRY TEXTILE SENSORS, AND ELECTRONICS INTEGRATION IN CLOTHING, BED SHEETS, AND PILLOW CASES FOR NEUROLOGICAL, CARDIAC AND/OR PULMONARY MONITORING

CROSS-REFERENCE TO RELATED APPLICATIONS

This application is a divisional of U.S. patent application Ser. No. 15/668,036, which is a continuation in part of U.S. application Ser. No. 13/657,854, filed Oct. 22, 2012, which is a continuation of U.S. application Ser. No. 13/415,698, filed Mar. 8, 2012, which claims the benefit of priority under 35 U.S.C. § 119(e) of U.S. Provisional Patent Application No. 61/450,423, filed Mar. 8, 2011, the entire disclosures of which are hereby incorporated by reference.

U.S. patent application Ser. No. 15/668,036 is also a continuation-in-part of U.S. patent application Ser. No. 13/829,898, filed Mar. 14, 2013 which is a continuation-in-part of U.S. patent application Ser. No. 13/449,755 filed Apr. 18, 2012, the entire disclosures of which are hereby incorporated by reference herein.

TECHNICAL FIELD

The present disclosure relates to electronic and optical sensor technologies, and their packing to enable their integration into textile. These sensor capabilities will enable the use of textile for health monitoring, while operating in contact or in proximity of person's body.

BACKGROUND

Chronic disease management and in-hospital patient care are two major contributors to healthcare costs. The former consists of patients in need of repeated tests to assess disease progression or protocols for drug dosage adjustments. The latter consists of patients recovering from surgeries or in need for constant observation for diagnosis. They contribute to approximately 30% ($690 billion) and 20% ($460 billion) of the annual healthcare costs, respectively, in the United States of America. See, e.g., Tabibiazar R., Edelman S. V., "Silent Ischemia in People with Diabetes: A Condition That Must Be Heard," Clinical Diabetes, Vol. 21 (1), 5-9 (2003), the disclosure of which is incorporated herein by reference.

Heart related ailments like coronary heart diseases, cardiovascular diseases, and strokes that are caused by clots or hypertension are the predominant causes of mortality in the US among both men and women. However, the number of deaths due to cardiac ailments in women has been consistently higher than in men since as early as 1985. In 2006, mortality due to all cardiac ailments among women was nearly 60% more than that due to all forms of cancer combined. This difference is also imminent in the case of postoperative survival among women after major cardiac surgeries like coronary bypass. At age 40 and older, 23 percent of women compared with 18 percent of men die within one year after a heart attack. This statistic has been related to the post-menopausal hormonal changes like the levels of estrogen in the blood. Estrogen has been known to have a prophylactic effect on the formation and growth of arterial plaques and clots, which can stifle the flow of blood through major blood vessels or stop it altogether. However, administration of Estrogen and Progestin has been shown to have minimal effect on the outcome of cardiovascular diseases in post-menopausal women.

Chronic diseases such as asymptomatic myocardial ischemia, a decrease in blood supply to the heart, appear as episodic events that do not leave any diagnostic evidence behind, making them all the more difficult to identify. Detection of Cardiac arrhythmias or irregular beats from continuous electroencephalogram (ECG) recordings is an important metric that physicians use to adjust medication for post myocardial infarction patients.

The major risk factors that have been reported to affect the cardiac health of women are smoking, inactivity, obesity, diabetes mellitus and hormonal changes resulting from menopause. Subtle changes in the cardiac activity manifested as irregular heartbeats, aberrational variations in the body's autonomous regulation of blood pressure and minor transient blockages in flow of blood to the heart, due to such chronic conditions or risk factors lead to fatal cardiac episodes. Thus, the best recourse is to engage in preventive measures involving continuous real-time monitoring to better track these physiological changes. Moreover, techniques like Electrocardiograph (ECG), blood pressure, heart rate variability analysis through time, frequency and wavelet domain analysis techniques have been successful in tracking the above-mentioned subtle changes.

More generally, vigorous exercise and exertion is known to increase the risk of Sudden Cardiac Death (SCD) in both men and women, including youths as well as adults, with underlying cardiovascular diseases (CVD). Recently, SCDs have been reported with a high rate of occurrence among athletes in soccer, football and basketball. Prescreening athletes with 12-lead Electrocardiograms (ECG) has been a successful measure to identify individuals at high risk for SCDs and exclude them from participation. The total cost for such prescreening of athletes is estimated to be in the order of $10B/year. The high risk of SCDs during training or exertion suggests that ECGs are of far greater value when acquired real-time during the actual training where abnormal cardiac electrophysiology can be tracked and identified before the onset of symptoms. The availability of such immediate diagnostic data would also significantly reduce the time taken to administer the appropriate resuscitation shock. What is needed is method for obtaining cardiovascular information in an unobtrusive manner so that participants in high-stress activities can be continuously monitored for abnormalities.

Cardiovascular diseases and neurological disorders form the majority of diseases that need constant or periodic medical attention. The concept of continuous health monitoring can be translated as point of care technology for preventive/corrective medicine and as metabolic rate estimation and regulation as a part of healthy lifestyle. Point of care technology aims at enabling diagnostics in hospice, at home or ambulatory (on the move).

Health monitoring textile is a type of wearable and ambient healthcare technology: an ensemble of non-invasive sensor systems, which operates in contact or in proximity of person's body. Resemblance to a conventional wearable item (apparel) or integrability in it increases the relevance of such a device. Wearable fabric based items like vests, socks, shorts, head bands, arm bands, wrist bands and caps, foot wear, and drapes like bed spreads/sheet and pillow covers can incorporate sensors for monitoring the health of an individual for diabetes, neurological, and cardiovascular monitoring.

Neurological disorders such as sleep disorders and sleep deprivation affect more than thirty million people, while another six million have moderate to severe sleep apnea in which breathing briefly stops. That is nearly one in five Americans, making sleep apnea as prevalent as asthma or diabetes. More than six million people have restless leg syndrome and periodic limb movement disorder which jolts them awake repeatedly. As many as twenty-five million people remain undiagnosed and untreated which will account for over $22 billion in unnecessary health care costs. Apart from physical factors such as obesity, studies have shown that the cumulative long-term effects of sleep loss and sleep disorders are associated with a wide range of serious health consequences and many life threatening illnesses including increased risk of hypertension, diabetes, depression, heart attack, impotence and stroke, to name a few. In addition, a significant percentage of severe traffic and industrial accidents may be caused by the involuntary human transition from wakefulness to sleep.

There are also apparent links between deficits in brain chemistry and obstructive sleep apnea (OSA) and REM sleep behavior disorder (RBD). Both are relatively common sleep problems that disturb the slumber and daytime behavior of millions of Americans. It has been reported that multiple system atrophy (MSA), a rare and fatal degenerative neurological disease, is almost always accompanied by severe sleep disorder. Patients with the fewest dopamine-producing neurons in the striatum of their brains had the worst RBD symptoms, talking and violent flailing during their sleep. People with OSA show tissue loss in brain regions that help store memory, thus linking OSA with memory loss and Alzheimer's disease. Obstructive sleep apnea, in which breathing temporarily stops during a person's sleep, often affects adults but goes undiagnosed in many cases. Its most notable symptoms are snoring and excessive daytime sleepiness, though it can also affect blood pressure, memory and even reaction-time while driving.

What is needed is a robust and nondisruptive monitoring bed sheets- and pillow cases-based system that addresses continuous biopotential measurements, which can analyze and record the required parameters while the patient is at home and sleeping in his or her own bed.

Textiles offer a durable platform for embedded sensor and communication systems, with the components like sensors and communication chip-sets stitched or woven into the fabric. Individual electronic components can be mounted on the textile and connected through electrical connects that have been built in or manufactured in the textile itself. The electronic functionality should be embedded while maintaining the textile properties of product like wearing comfort and durability. Manufacturing techniques used for such smart textiles have to be compatible with existing textile manufacturing techniques to minimize additional costs.

Physiological signals, such as but not limited to, Electrocardiogram (ECG), Pulse rate (and heart rate variability), blood pressure, Electroencephalography (EEG), electro-oculography (EOG) and electromyography (EMG), provide a comprehensive medical status of a person. In combination with wireless communication technology, they can be used for remote medical diagnosis or prognosis. Textile based dry electrodes with lower electrode-skin contact impedance for improved performance in bioelectric signal acquisition is important to achieve un-obstructive and long term health monitoring. This is not possible with conventional wet electrodes due to drying of the conductive gel over period of time that leads to loss of functionality and skin irritation. Un-obstructive blood pressure monitoring requires an alternative to the conventional inflatable cuff based sphygmo-manometer. Also, such a setup is difficult to incorporate in textile and very energy intensive for mobile health monitoring.

SUMMARY

Printing processes can be used for making complex high resolution designs on a wide range of substrate, including textile. See, e.g., Sherman, R., "Could Printed Electronics Replace Traditional Electronics?" Printed Circuit Design & Fab, 27 (3), 38, 40, 42 (2010), the disclosure of which is incorporated herein by reference. Printing allows for direct pattern transfer of electronics with little or no waste of material and thus a cost effective alternative to photolithography techniques. Among the popular printing technologies, screen printing and gravure are well suited for mass produced electronics on textile because of their parallel printing technology and the substrate handling. See, e.g., Sheats, J., R., Biesty, D., Noel, J., Taylor, G., N., "Printing technology for ubiquitous electronics," Circuit World, 36 (2), 40-47 (2010); Kah, B., E., "Printing methods for printed electronics," 24th International Conference on Digital Printing Technologies. Digital Fabrication 2008, 15-20 (2008), the disclosures of which are incorporated herein by reference.

Parallel printing, as compared to serial printing technologies like ink jet printing, has a higher manufacturing throughput. Screen printing and gravure printing technologies do not deviate significantly from garment making techniques making them cost effective. These technologies will enable fabrication (over a large surface area) of electronics with varied functionality like:—sensor systems and flexible printed circuits for electrical connections between sensors and the embedded wireless telemetry systems.

The textile based healthcare applications and packaging technology described in accordance with embodiments of the present invention provide improved sensor performance and seamless integration of the sensor systems in the textile for un-obstructive health monitoring. The technologies use a novel combination of nanomaterials and textile fabric for sensor and packaging electronics, provided in a garment, bedsheets, pillow cases or arm bands.

According to various aspects of the disclosure, sensors mounted on a textile include at least one of electrically conductive textile electrodes; single or multiple optically coupled infrared and red emitter and photodiode or photo transistor; and thin film or Resistive Temperature Detector (RTD).

According to the disclosure, textile electrodes, electrical connections, and electrical functionalization use at least one of nanoparticles, nanostructures, and mesostructures. As used herein, electrical functionalization includes textile integrated sensors, electrical signal carrying lines, electrical connections, and analog and digital components.

In accordance with some aspects of the disclosure, conductive thread, for electrical connections, may include a fiber core made from nanoparticles and mesoparticles made of conductive materials such as but not limited to metals, alloys, and graphine structures, and a sheath of insulating materials such as but not limited to nylon, polyester, and cotton.

Also disclosed herein are embodiments of a wearable remote electrophysiological monitoring system which includes a fully wearable textile integrated real-time ECG acquisition system with wireless transmission of data for the continuous monitoring of football players during training and on the field during games. The system is applicable also to basketball players, soccer players and other athletes, as well as members of high-stress occupations such as military personnel, police, firefighters, and various other emergency responders.

To that end, the sensors required to pick up the necessary biological signals and constantly relay the signals need to be seamlessly integrated into everyday clothing such that no additional preparation or mounting of individual sensors is needed. The innovative 'e-bra' described here is a foundation garment or a brassiere, designed with a multitude of sensor capabilities for cardiac and pulmonary health monitoring which are integrated into a fabric with improved performance. The end result is an autonomous garment that can collect and transmit vital health signals of the wearer.

The e-bra will also help non-critical users (i.e. those not acutely suffering from a condition such as heart or pulmonary diseases) for monitoring important metrics such as calories burned during a workout, to get an optimum workout by jogging or on a treadmill, and pacing their exercise. For instance, the wearer's heart rate should be at the proper intensity level for an extended period of time. If the heart rate gets too high, the wearer's activity can become counterproductive. If it is too low, the wearer is not getting optimal health benefits. This technology will thus monitor and provide the optimum workout needed for a given individual.

The e-bra system described here is a comfortable and wearable monitor for cardiovascular and pulmonary health for women. It has a basic structure of a foundation garment for woman's bosom that covers all or part of chest, shoulders, arms and upper back. Sensor components include biopotential electrodes like electrocardiogram (ECG) electrodes which are mounted on the garment, photoplethysmography channels which are worn as an arm band, piezoelectric acoustic sensors, temperature sensors, and piezoresistive respiration effort sensors.

This technology also provides additional benefits even if one is not a cardiovascular or pulmonary patient. For example, individuals could use the devices to report beneficial activities (exercising, taking medications, sleeping) and receive incentives from partners (doctors, insurance companies, social networks) with whom they share that information.

Thus, in one embodiment the invention provides a wearable remote electrophysiological monitoring system. The system includes a garment having at least one nanostructured, textile-integrated electrode attached thereto; a control module in electrical communication with the at least one nanostructured, textile-integrated sensor; and a remote computing system in communication with the control module.

In another embodiment, the invention provides a system for cardiac monitoring of an individual. The system includes a garment having a plurality of nanostructured textile electrodes integrated therein, the electrodes arranged on the garment to record data for an ECG of the individual; a first controller electrically coupled to the plurality of electrodes, the controller including a wireless transmitter, the first controller being configured to collect the recorded data for the ECG from the plurality of electrodes and to cause the wireless transmitter to wirelessly transmit the recorded data; and a wireless receiving station including a wireless receiver and a second controller, the second controller configured to cause the wireless receiver to receive the recorded data transmitted by the wireless transmitter, analyze the recorded data for the ECG, analyze the recorded data, identify an abnormality in the ECG, and generate an alert if an abnormality in the ECG is identified.

In yet another embodiment, the invention provides a system for cardiac monitoring of a group of individuals including a plurality of wearable monitoring units. Each wearable monitoring unit includes a garment having a plurality of nanostructured textile electrodes integrated therein, the electrodes being arranged on the garment to record data for an ECG of the individual; a first controller electrically coupled to the plurality of electrodes, the controller including a wireless transmitter, the first controller being configured to collect the recorded data for the ECG from the plurality of electrodes and to cause the wireless transmitter to wirelessly transmit the recorded data. The system also includes at least one wireless receiving station including a wireless receiver and a second controller, the second controller configured to cause the wireless receiver to receive the recorded data transmitted by the wireless transmitter and to analyze the recorded data for the ECG, the second controller further configured to analyze the recorded data, identify an abnormality in the ECG, and generate an alert if an abnormality in the ECG is identified.

BRIEF DESCRIPTION OF THE DRAWINGS

Embodiments of the invention can become more fully understood from the detailed description given herein below and the accompanying drawings, given by way of illustration only and thus not intended to be limitative of the present invention:

FIG. 4 is a graph showing the signal from an exemplary 3-Lead ECG dry textile electrodes system with leads 1, 2, and 3 plotted simultaneously;

FIG. 5 is a graph of a leading electrocardiograph (lead 2) and lagging brachial artery pulse data acquired on the same time line for measurement of pulse transit time;

FIG. 6 is a graph showing calibration curves for systolic and diastolic blood pressures versus pulse transit time;

FIG. 7 is a graph illustrating a Resistive Temperature Detector based temperature sensor calibration curve; and FIG. 8 is a graph of brain rhythm such as Alpha, Beta, Theta and Delta waves from a textile sensor in pillow cases and bed sheets

FIG. 16 shows statistics on cardiac related mortalities in females as compared to females in the United States: 1976-2006.

FIG. 17(a) shows placement of electrodes for ECG lead 2.

FIG. 17(b) shows an ECG waveform with characteristic P wave, QRS complex, and T and U waves.

FIG. 26 (a-d) shows components of a wireless ECG monitoring garment system, wherein

FIG. 31 shows SEM photographs of (A) thiol functionalized polymer capped silver nanoparticle and (B) pure silver nanoparticle.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

An electrode design for electrophysiological sensing (ECG, EEG, etc.) is developed as a electrically functionalized piece of fabric mounted on a spring mechanism. The electrode fabric is dyed with conductive ink, or enmeshed/decorated with conductive nanoparticles. The electrode surfaces have been engineered to have nanoscale and mesoscale free standing conductive structures. This is done to increase the effective surface area of the electrodes. Electrode surface area, which is in contact with the skin, is important to the signal quality. The signal measured is electric potential across the load resistance between the two electrodes that can be conceived as the impedance due to body bulk, skin and electrodes. Large electrode surface area results in low skin-electrode contact resistance. The free standing structures are deposited on the above mentioned conductive fabric by flocking electrically conductive fibers. Another technique is printing the electrodes with nanocomposite ink, which will have nanostructures on the surface of the printed thick film for increase surface area. Printed electrode for Electrocardiography (ECG, EEG etc.) is a technology based on the fabric itself. The electrodes system printed on the textile serves for multi-lead ECG signal acquisition, when the electrode surface is in contact with person's skin. The composition of the ink will be described in more detail below.

Figure 1:
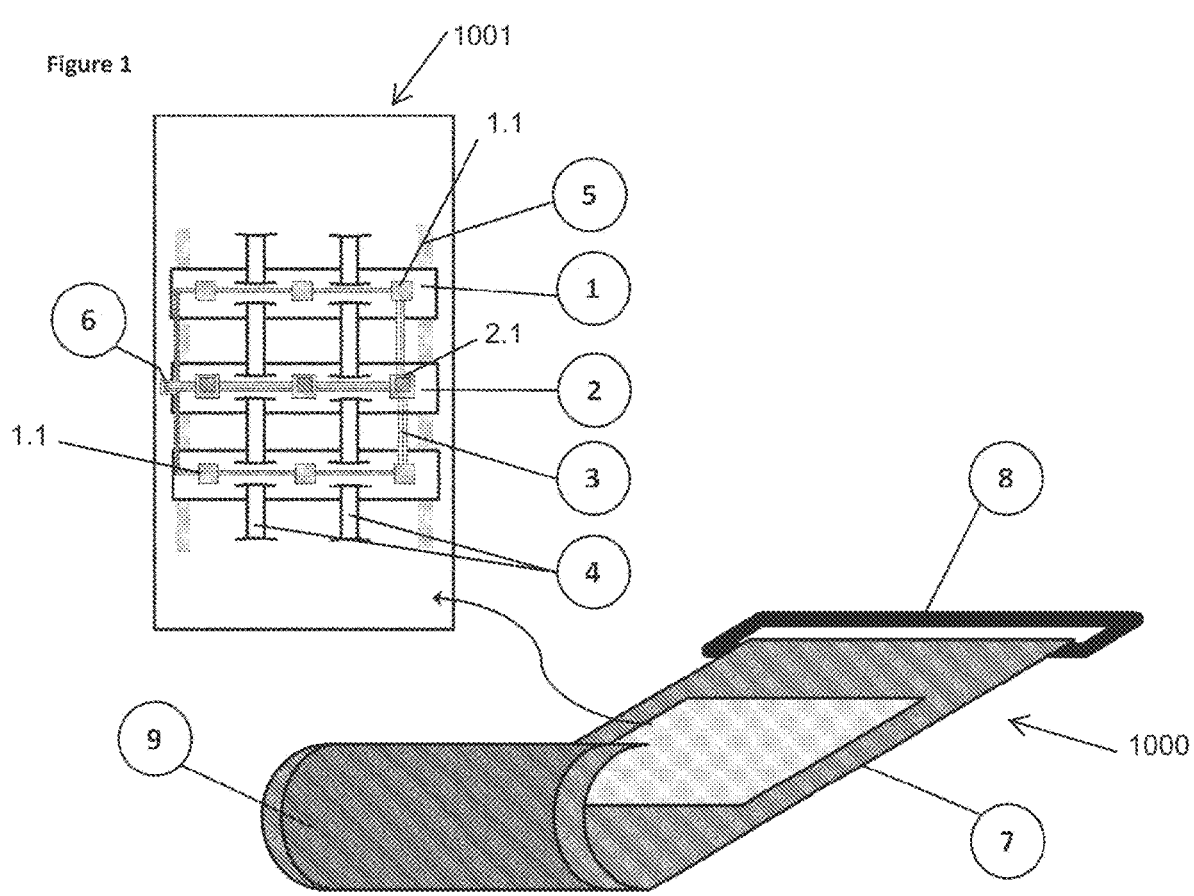
FIG. 1 illustrates a design of an exemplary arm band for brachial artery plethysomography in accordance with various aspects of the disclosure.
Figure 2:
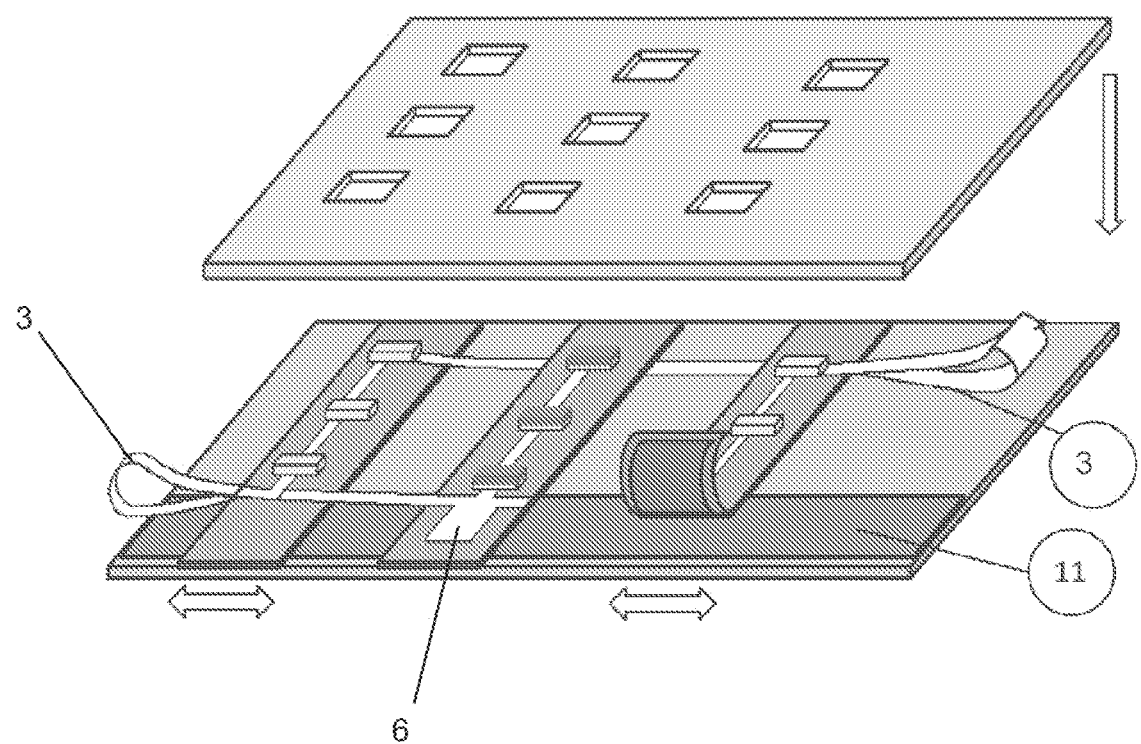
FIG. 2 illustrates an exemplary mechanism for adjusting the relative positions of the sensors according to various aspects of the disclosure.

FIGS. 1 and 2 illustrate the design of an arm band 1000 for brachial artery plethysomography. The arm band 1000 includes a multichannel infra-red emitter-detector system 1001 which includes optically coupled infrared emitters 1.1 and photodiode detectors 2.1 arranged in arrays and connected to a breakout plug that can be connected to the primary circuit on the textile. Blood pressure measurement system is an opto-electronic system, plethysmograph (PPG) that monitors the blood flow in the brachial artery in the left arm. The multichannel infra red emitter-detector system 1001 on the arm band 1000 is placed on the left on the axis of the brachial artery (inside part of the left arm) to detect change in blood flow of the brachial artery. The system is used in combination with the ECG measurement to estimate the time it takes for the pulse, pulse transit time (PTT) to move from the aortic valve to the PPG site. The PTT is an index for estimation of arterial blood pressure (ABP). The PPG system uses infrared reflectance by the blood for monitoring the blood flow volume. Positions for the emitter arrays 1 (including emitters 1.1) and the detector array 2 (including detectors 2.1) are important to get the optimum reflectance signature.

FIG. 2 illustrates the mechanism for adjusting the relative positions of the sensors (emitters 1.1 and detectors 2.1). The sensors positions can be changed by sliding the emitter arrays 1 on a spin and securing them by hock and loop to accommodate for different arm diameters. The size of the arm varies from person to person. To address this issue, provision for adjusting the array spacing has been provided. The emitters 1.1 and detectors 2.1 are surface mounted devices (SMDs). They have been soldered on to a flexible printed circuit 3 with flat flexible connections running between components. This is to enable packaging of the components in a textile based arm band. The components are arranged in three arrays. Array in the middle is stationary, while the flanking arrays can move on two spines 4. The system uses hookand loop arrangement 11 to secure the arrays in position. The band system has been designed as a detachable component of the textile health monitoring system. A flat flexible connection port 6 is provided on the band for connection to ancilliary or master circuit for power supply and signal relay. The use of flexible printed circuit is to enable packaging of the components in a textile based arm band 7 with a buckle 8, and hock and loop 9 for strapping around the arm.

Figure 3:
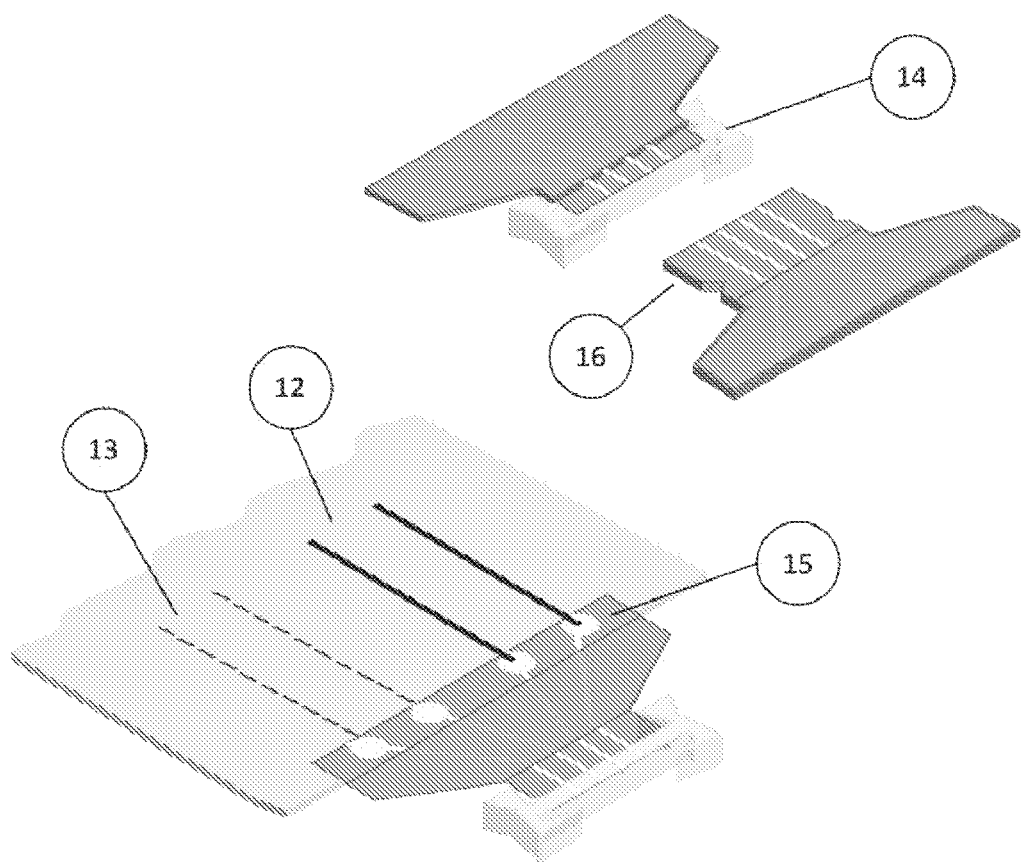
FIG. 3 illustrates an exemplary packaging technology for the sensors in accordance with various aspects of the disclosure.

FIG. 3 illustrates the packaging technology for the sensors. The textile based electric connection lines for the sensors are linked to the break out pins of a socket. The figure depicts the socket with thread as well as printed lines on fabric. The corresponding plug is mounted on the electronics for wireless communication and power supply. A similar concept is used for connecting the arm band electronics to the master circuit. Printed electrical connects, on the textile fabric, can function like a flexible textile based printed circuit film. This will act as a system to facilitate packaging of the sensor systems, and amplifier-transmitter electronics in the textile. (FIG. 3) The connect lines or conductive traces 12 use nanomaterial composite based inks. The binder itself can serve as printing ink, so that the conductive traces can be insulated by an overlay of traces made with binder only. The ink formulation uses modified acrylic, epoxy or resin binders with conductive nano particles and nanostructures dispersed in it. The nanocomposite based conductive patterns provide electrical properties similar to conductive metal wires or strips, while being able conform with the flexibility of textile. Binder's adhesion properties allow for printing on nylon, cotton, lycra, spandex, neoprene or other elastomeric fabric or film. The binder possesses high elasticity; therefore, it will protect the traces from disruption due to stretching of the fabric or film.

Textile based connections for packaging of sensor and wireless electronics in textiles, can be accomplished with conductive threads 13. The textile health monitoring system also uses conductive threads made of conductive fiber core and an insulation sheath. Conductive fiber core can be made of nano fibers or meso fibers made of metals like silver, copper, titanium; alloys like stainless steel, nickel-cromium; and graphine structures like carbon nanotubes. The sheath can be made of nylon, polyester, and cotton. These threads are compatible with machine weaving. In addition to being compatible with textile platform, the printed connections and conductive threads are resistant to triboelectric effect. This prevents build up of static charge, which occurs when wearing textile products. Thus, signal artifacts due to static charge build up are avoided.

The printed connections and conductive thread connections are required to be able to connect to the electronics for wireless communication and power supply. While these components are not made on textile substrate, their electronic connects do not readily interface with the textile based connects. The textile health monitoring system uses a special electronic connector assembly (FIG. 3), which houses a socket 14 with break out pins attached to corresponding textile connects 15 with rivets, crimps or silver epoxy. The socket is compatible to the plug 16 on the electronic module for wireless communication and power supply.

Figure 14:
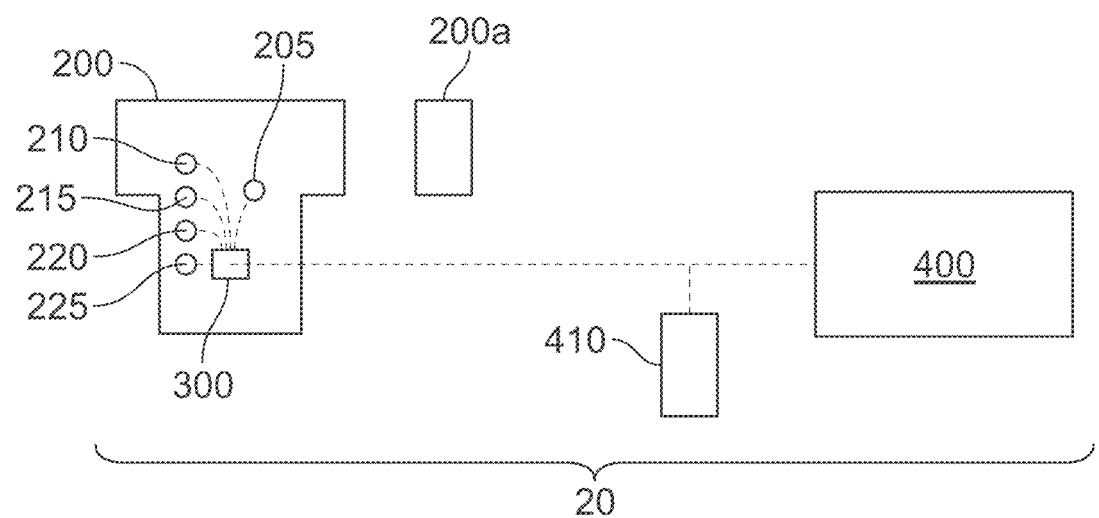
FIG. 14 shows a block diagram of an embodiment of the system.

In various embodiments, the invention includes a wearable remote electrophysiological monitoring system 20 (FIG. 14). The system 100 may include a garment 200 having at least one nanostructured, textile-integrated electrode 205 attached thereto, a control module 300 in electrical communication with the at least one nanostructured, textile-integrated electrode 205, and a remote computing system 400 in communication with the control module 300 (FIG. 14).

The system may also include a plurality of physiological sensors such as a photoplethysmography sensor 210, an acoustic sensor 215, a temperature sensor 220, and a strain sensor 225 (FIG. 14). The acoustic sensor 215 may be attached to the garment 200 to collect acoustic signals from a heart of a wearer of the garment 200. The temperature sensor 220 may include a resistive temperature detector, a thermistor, and an infrared photodiode detector. The strain sensor 225 may include a piezoresistive respiration effort sensor to monitor breathing of a wearer of the garment 200. The various physiological sensors may be electrically connected to the control module 300 by silver-coated thread, conducted traces, nanocomposite inks, or other techniques described herein. Each group of electrodes or sensors may have an amplifier module associated therewith, for example attached to the garment 200 in the vicinity of the electrodes or sensors or incorporated into the control module 300.

The remote computing system 400 may communicate with the control module 300 using radio-frequency communications, for example using short-range communications such as Bluetooth; a local area network (e.g. wi-fi); satellite; or cellular communications technology. The remote computing system 400 may also communicate with the control module 300 using other forms of communications such as infrared light or microwaves. In some embodiments, the remote computing system 400 may communicate with the control module 300 using a wire-based connection or a combination of wired and wireless modalities.

The nanostructured, textile-integrated electrodes 205 may be made of a hierarchically-organized nanostructure sheet with vertically standing nanowires/filaments. The electrodes 205 are generally incorporated in the fabric of the garment 200 with an elastic backing for concomitant contact with the skin.

The nanostructured, textile-integrated electrodes 205 include nanostructures 207 attached to and projecting from electrically-conductive fibers 209 that may be incorporated into a portion of fabric. The nanostructures 207 may project from the fiber 209 to varying lengths ranging from 0.01-10 micrometers, and in one embodiment project from the fiber 209 less than one micrometer. The portion of fabric may then be attached to or otherwise incorporated into the garment 200 and placed into electrical communication with the control module 300.

Figure 15:
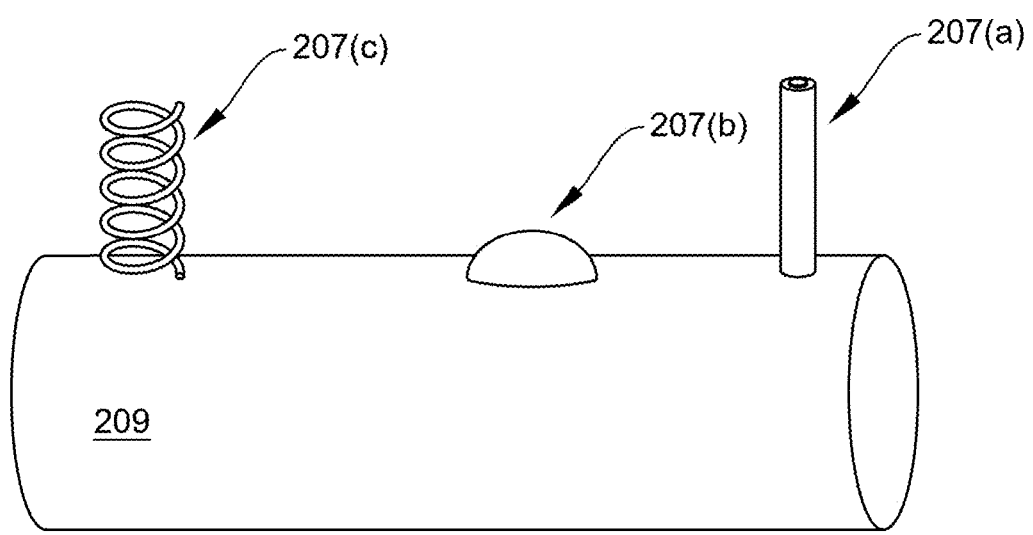
FIG. 15 shows nanostructures projecting from a fiber.

The nanostructures 207 projecting from the fiber 209 may have different shapes and form factors and may include one-dimensional nanostructures 207a, two-dimensional nanostructures 207b, and/or three-dimensional nanostructures 207c (FIG. 15). The one-dimensional structures 207a may include approximately linear structures such as wires or tubes. The two-dimensional structures 207b may include shapes such as bumps or bubbles. The three-dimensional structures 207c may include shapes such as helices. The helices are particularly suitable as they have a large surface area available for making contact with a wearer's skin. In some embodiments in which helical structures are employed, a particular handedness of the helices (e.g. left-handed or right-handed) may produce better results such as improved conductivity. The fiber 209 from which the nanostructures 207 project is typically electrically conductive, which may be achieved by using a fiber 209 that is coated with an electrically conductive material (e.g. silver) or by using a fiber 209 that is blended or intertwined with an electrically conductive material (e.g. silver). The nanostructures 207 may be fabricated from a number of different materials such as gold, silver, steel, or textiles. In one embodiment, a piece of fabric having fibers with nanostructures thereon can have a density of between 10,000 and 100,000 nanostructures per square centimeter of fabric.

In various embodiments, the nanostructured, textile-integrated electrodes 205 are used as dry contact sensors, i.e. sensors that do not require a conductive gel or other substance to be used with the electrodes 205 to make electrical contact with the wearer's skin. The base substrate (e.g. fiber 209) is flexible and conductive and can be made of metal or metal-textile blend(s) or metal-polymer blend(s). Possible metals that may be used include gold, silver, titanium, platinum, and steel or a steel alloy, and possible textile fabrics that may be used include nylon, silk, Lycra, spandex, polyester, modified celluloses, and cotton.

The substrate can be made of flexible fabric made of natural yarns such as cotton, silk; polymer based yarn such as polyester, polyester lycra blend, nylon, rayon; metallic yarn such as stainless steel; fabrics with coatings of electrically conductive material such as silver, polyaniline; fabrics coated with polymer film to reduce surface roughness.

The nanofibers can be vertically standing structures attached to the substrate by an adhesive layer of materials such as polyurethane, polyvinylchloride.

As the fabrics in the substrate and nanofibers may be damaged and/or burned by high temperature processing, it is important to use processes with a processing temperature below 300 C.

Nanosensor fabrication techniques such as nano-imprinting (described below) and template assisted growth of nanostructures (such as for gold nanowires) are low temperature processes, which require processing temperatures of less than 300° C. Inasmuch as fabrics can withstand temperatures far below most deposition process temperatures, the lower end of the processing range is not of particular interest. However, it is noted that fabrics can typically withstand temperatures as low as −20 C.

Exemplary processes include processes described in commonly owned U.S. Ser. No. 14/995,334 entitled Large Scale Manufacturing of Hybrid Nanostructured Textile Sensors, filed Jan. 14, 2016, U.S. Ser. No. 15/425,302 entitled Large Scale Manufacturing of Hybrid Nanostructured Textile Sensors, filed Feb. 6, 2017, U.S. Ser. No. 15/425,360 entitled Roll-to-Roll Large Scale Manufacturing and Electronics Integration Process of Wireless Nanosensor Systems for Human Health Monitoring, filed Feb. 6, 2017.

Nanoimpring techniques can also be used. In particular, a nanoimprint drum is made by patterning a flexible nickel foil. Flexible nickel foil can be wrapped around the drum in the roll to roll machine. Nano imprint lithography is introduced through a roll to roll or a mechanical machine, which imprints patterns on the substrate or polymers. The substrate can be a nanocomposite ink that is coated on flexible substrate such a textile fabric. The ink is cured after pressed by the imprint drum thus form free standing nanostructures. A unit silicon stamp, with the required pattern, is fabricated to transfer the pattern on to a master stamp to increase the yield of the stamps in the nickel foil. The patterned master stamp is then used to imprint the patterns on the nickel foil which is finally wrapped around the drum. The unit silicon stamp is first fabricated by electron beam lithography that enables the writing of small patterns onto the resist and finally making patterns into the silicon substrate by dry etching. The preheated unit stamp to press on the resist film on a silicon substrate. The stamp is cooled and pulled up. The sequence is repeated in the new location on the resist film. The polymer is imprinted at elevated temperatures, at which the viscosity is relatively low and the polymer is able to flow under pressure. The stamp is cooled below the glass transition temperature before releasing the pressure and separation. The stamp is then moved to the next site and the process is repeated. Thus making a large surface of the same pattern on a large area of resist film. This serves as a patterned mold for nickel foil fabrication. The patterned polymer mold is sputter coated by the TiW/Cu layer, which serves as a seed metal layer. This metal layer provides electrical contact for nickel deposition in the electroplating bath. After electroplating the foil is released from the mold by dissolving the mold.

Gold nanowires can be made by using a template assisted growth by electro-deposition. The gold nanowires are grown on a conducting substrate such as conductive metallic film coated textile. The gold nanowires are grown using a non-porous template made materials such as polycarbonate membrane. The density of nanopores is about densities of 103-108 per square centimeter. The nanowires have diameter between 20 nm and 200 nm and are present at densities of 103-108 per square centimeter. The electro-deposition process is done by laminating the template on the conductive textile substrate at the desired location and dipped in a tank of gold salt such as sodium gold sulfonate. A potential of 0.6±0.05 V was applied across the template-substrate stack and platinum wire mesh. The applied potential can be varied to obtain optimum rate of deposition. Free standing gold nanowires are obtained by removing the polycarbonate film. Reference is also made to U.S. Pat. No. 8,348,841, incorporated herein by reference in its entirety.

Vertically standing polymer nanofibers can be made of a polymer material selected from the group consisting of polyethylene terephthalate, polyethylene naphthalate or polybutylene terephthalate. The polymer nanofibers can also be made of a polyester. The polymer nanofibers can also be made of a polyurethane. The polymer nanofibers can also be made of a material selected from the group consisting of polystyrene, polyvinyl alcohol, ethylene vinyl alcohol, polyacrylamide or poly lactic acid. The polymer nanofibers can also be made of a polyethylene terephthalate modified with sulfonated isocyanate.

These nanofibers can be coated with films of different properties. The film can be a conductive material selected from the group consisting of silver, gold, platinum, polyaniline, polypyrrole, poly(3,4-ethylenedioxythiophene). The film can be a metal oxide film such as titanium oxide, iron oxide. The film can be a piezoelectric material film such as zinc oxide.

The fabric surface needs to be sufficiently leveled for achieving proper adhesion of printed or deposited nanomaterial(s). In particular, the fabric surface must be leveled to a roughness that is below 100 nm. Leveling of the surface can be achieved by printing polymer films of materials such as poly vinyl chloride, poly urethanes, polyethylene napthanate and polyethyl terphthalate. Multiple polymer layers can be stacked, while progressively changing viscosity of polymer printing ink. This levels the fabric surface by filling the surface features.

In particular, the polymer layer can be printed or spray coated, and cured. The liquid containing monomer, polymerizing catalyst and solvent will fill the gaps between fibers/filaments that make the textile fabric. The filling process may require repeated printing/coating and curing steps depending on the size of the gap. Higher viscosity film tends to form the base by sufficiently wetting and adhering to the textile fabric. But film conforms and shows same roughness as the textile fabric surface. Subsequent printing/coating with liquid of lesser viscosity achieves filling up of the gaps and forming a smooth layer. A slow curing process (at a temperature, for example from about 100 C to about 130 C) allows for gradual evaporation of solvent and provide a defect free surface.

In various embodiments, the garment 200 may be a brassiere (also referred to as the e-bra), a vest, a shirt, or other garment worn over the upper body. In general the garment 200 is form-fitting in order to ensure sufficient contact of the various sensors with the skin of the wearer. Generally, the garment 200 conforms to the wearer's body and complies with standard sizing/fitting schemes, including, in the case of an e-bra, standard cup size and strap lengths. Suitable materials for making the garment 200 include nylon, silk, Lycra, spandex, polyester, modified celluloses, cotton, and combinations of these and other materials, and in general the garment 200 is washable. As described herein, the garment 200 includes electrodes/sensors incorporated therein and in some embodiments the garment 200 may be supplemented by one or more armbands 200a (FIG. 14) or other wearable devices for collecting additional data. In various embodiments, the system 20 may be worn underneath the wearer's normal clothing for seamless deployment for monitoring the wearer's cardiovascular health or other health indicators.

In some embodiments, the system 20 includes a plurality of nanostructured, textile-integrated electrodes 205 arranged on the garment to collect an electrocardiogram (ECG) signal from a wearer of the garment 200 (FIGS. 9-11), where the electrodes 205 are located on the garment 200 so as to capture heart activity from different perspectives or positions. Since the electrodes 205 in certain embodiments are textile-based, they can be more readily integrated into the fabric of the garment 200 (e. g. an e-bra).

Wireless Communication Platform:

Coupled with a low power microcontroller and Bluetooth module (Zigbee, WiFi and other communication protocols as appropriate), the sensor data can be streamed to commercial off-the-shelf cell phones and smart phones, laptops, computer, and handhelds units. A software system has also been developed for cellular 'smartphones' that can collect sensor data over Bluetooth and can relay data over 3G, Wi-Fi, WiMax or any outgoing connection with RFID. Apart from the cost benefits of using an off-the-shelf cell phone for data relaying, our software system will provide two other distinguishing features. First, it will implement filtering algorithms on the cell phone to mitigate issues due to motion and other artifacts, rendering clean data. It will provide a visualization interface at the cell phone through which users can see salient features of their heart activity such as heart rate. The software on the phone will run simple machine learning algorithms to perform preliminary anomaly detection. In case of an emergency, it can either alert the user and recommend him/her to hospital locations near his/her present location or make an automated call to the patient's physician with his/her present location. Thus caregivers can access into vital information anywhere and at anytime within the healthcare networks. The Zigbee based WiFi system used is capable of handling 65,000 patients at a given time.

The geo-tagged data is transferred to a cloud cluster and stored in a secure database and SD card. For physician diagnostics we will provide a new backend service, where the doctor can log into our system and can visually look at past ECG, EEG and other related data from the user or real-time continuous data (whichever is deemed necessary). If the physician desires, he/she can use our machine learning services to detect anomalies in the data that was collected in the past. In the event that our machine learning algorithms detect abnormalities in the data, our VoIP service can make phone calls or send SMS messages to physicians.

The example presented in FIG. 4 is to illustrate the ability of the smart textile health monitoring system to acquire 3 lead ECG signal using dry textile electrodes. ECG acquired here are Lead 1—between augmented right arm and augmented left arm, Lead 2—between augmented right arm and augmented left leg, and Lead 3—between augmented left leg and augmented left arm. This basic form of ECG acquisition monitors the atrial activity and ventricular activity of the heart. The data is also used for heart rate calculation and arterial blood pressure estimation.

The example presented in FIGS. 5 and 6 illustrates the blood pressure estimation application. While FIG. 5 shows the concept behind calculation of the pulse transit time (PTT), FIG. 6 shows the calibration curves used as the transducer functions for estimation of atrial systolic and diastolic blood pressure from PTT.

The example presented in FIG. 7 illustrates the body temperature sensing application of the flexible thin film temperature sensor. The calibration curve is used as a function by the signal acquisition software for converting the change in resistance of the thin film channel to temperature. The range of linear response is 32° C. to 38° C., which is the range of the temperatures observed at the axilliary location of the arm. The axial temperature range that covers from normal condition to feverish. See, e.g., Lodha, R., Mukerji, N., Sinha, N., Pandey, R., M., and Jain, Y., "Is Axillary Temperature an Appropriate Surrogate for Core Temperature?" Indian Journal of Pediatrics, 67 (8), 571-574 (2000), the disclosure of which is incorporated herein by reference.

The examples presented in FIG. 8 are typical brain rhythm as measured by the textile based sensor system. They are consistent with the regular wet gel electrodes used in the hospital. See, e.g., Allan Rechtschaffen and A. Kales, A manual of standardized terminology, techniques and scoring system for sleep stages of human subjects, Brain Information Service/Brain Research Institute, University of California, Los Angeles, Calif. (1977), the disclosure of which is incorporated herein by reference.

Exemplary ECG System

Figure 9A:
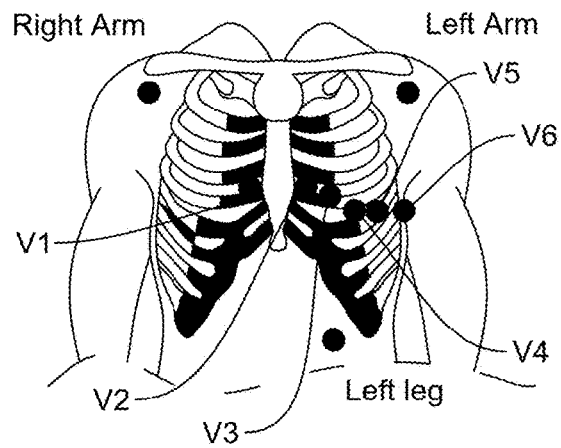
FIG. 9(a) shows lead placement for a twelve-lead ECG with derived limb leads.
Figure 9B:
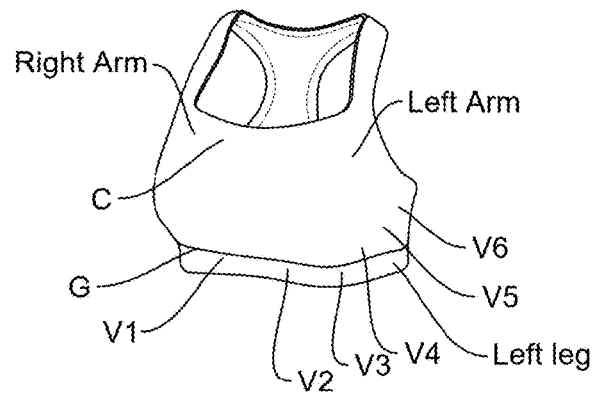
FIG. 9(b) illustrates the placement of electrodes on the frontal side of the garment in which the electrodes have been placed according to the medical specifications for the limb leads, precordial leads, chest lead, and ground lead.
Figure 9C:
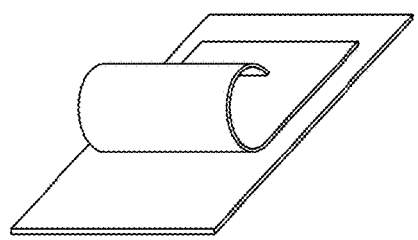
FIG. 9(c) illustrates the mounting of an electrode on elastic backing using stitching.

Although there can be variations in the arrangement of electrodes for measuring an electrocardiogram, the positions used in the embodiment depicted in FIGS. 9(a)-9(c) are medically classified as (but not limited to): limb leads: Right Arm, Left Arm, and Left Leg; precordial leads V1-V6; chest lead C; ground G; and experimental lead E at the back (shown in FIG. 10). In one embodiment, the electrodes 205 have conductive fiber-based connections, without using conventional wires, which enable the electrodes to send signals to an on board amplification and transmission system (e.g. which may be integrated into the control module 300).

Plethysmography measurements can be obtained from impedance measurements (as opposed to optical-based photoplethysmography measurements disclosed herein) in conjunction with ECG recording. This provides information regarding pulse transit time from ventricular discharge to the passage of the pulse at the brachial artery site, the brachial artery being located in the upper arm. The pulse transit time bears a correlation with the compliance of the brachial artery; therefore, it can be correlated to the blood pressure in the artery, thus accomplishing a unique non-invasive blood pressure measurement in real time on a continuous basis without the need for an inflatable cuff.

Figure 12:
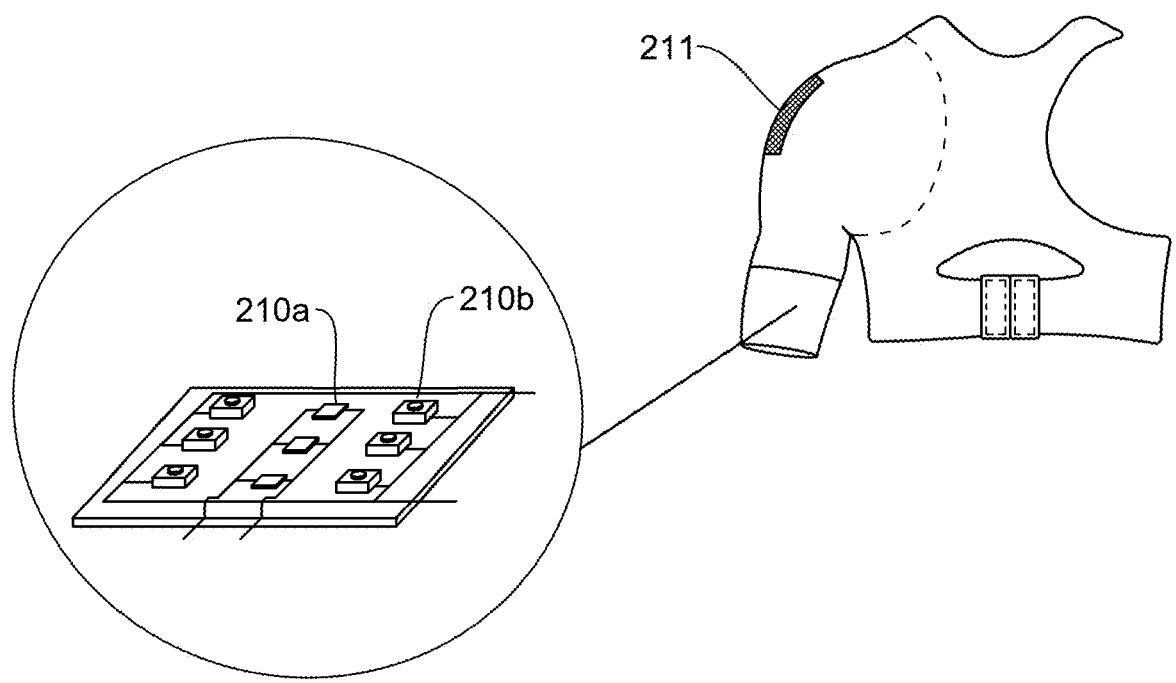
FIG. 12 shows the back side of a complete brassiere system, with an extended left arm sleeve that can be detached, with the inset showing a photoplethysmography module.

The system 20 may also include a plurality of photoplethysmography sensors 210 or channels, which may be integrated into the garment 200 or coupled to an armband 200a to be worn by the user (FIG. 14). In one embodiment, the photoplethysmography (PPG) channels use combinations of light emitting diodes (LED) 210a and photo detectors (PD) 210b (FIG. 12, inset) that are mounted on the garment 200 (particularly if the garment includes sleeves) and/or an armband 200a, where the armband 200a may be made of a material such as nylon, cotton, Lycra, spandex, neoprene, or other elastomeric fabric or film. The wavelengths of light that are used are generally biocompatible red and infrared. The origin of the observed PPG signals maybe due to absorption of the light that is emitted by the LED 210a or may be the reflection of light from the LED 210a by blood.

As with impedance-based plethysmography measurements, photoplethysmography measurements can be used to detect pulse waves in the brachial artery. The LEDs 210a may be arranged in a serial connection and the photo detectors 210b arranged in a parallel connection. The LED-PD combinations include two LEDs 210a flanking one PD 210b (FIG. 12, inset) at separations that constitute a solid geometric angle for optimum detection of the reflected or transmitted light from the deep-seated brachial artery. The combination is designated as one channel that is mounted in the transverse sense to the left brachial artery axis (inwards of the left arm). More than one such channel is used to scan the brachial artery. Such a configuration gives a stronger signal, one that is more tolerant to variations in the placement position of the arm band 200a or sleeve of the garment 200. As discussed above, the use of an armband 200a may be an addition to the system 20 for enhancing monitoring capabilities. In some embodiments in which the garment 200 includes sleeves, the photoplethysmography sensors 210 may be attached directly to the garment 200, in particular to the sleeves.

In those embodiments employing acoustic sensors, the acoustic sensors 215 may be based on a hydrophone pad design. The acoustic sensors 215 may be mounted on the garment 200 (e.g. e-bra) in a position that is suitable for detecting sounds being produced by activity of the heart and/or breathing of the wearer. The signals, recorded through these acoustic sensor 215 systems, are important for diagnosing medical conditions like heart murmur, heart valve activity, respiratory blockages, and subsonic (less than 20 Hertz) and ultrasonic (greater than 20 kilohertz) vibrations of diagnostic value. Piezo-resistive textile-based or textile-integrable strain sensors 225 may be mounted on the garment for detection of thoracic distention towards monitoring the respiration effort and respiration cycle.

In some embodiments, one or more temperature sensors 220 may be mounted on the garment 200. Temperature sensors 220 may be based on resistive temperature detectors, thermistors, or infrared photodiode detectors. As with other electrodes and sensors described herein, the temperature sensors 220 may have conductive fabric- or thread-based connections, i.e. without traditional wires, that enable them to send signals to an onboard amplification and transmission system (e.g. which may be integrated into the control module 300).

Figure 10:
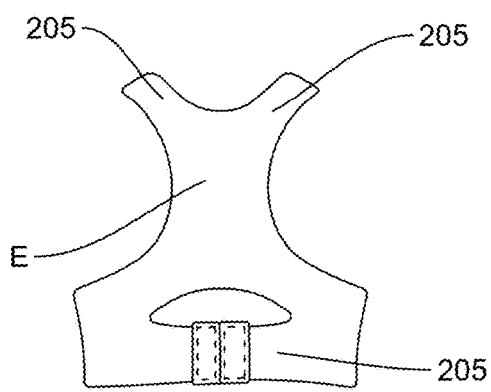
FIG. 10 illustrates the back electrode site and the elastic backings provided in the brassiere platform where the elastic backings facilitate the ECG electrodes maintaining contact with the skin.
Figure 11:
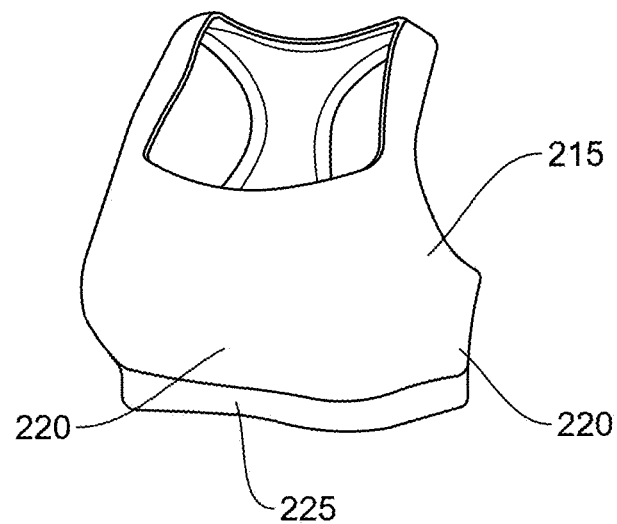
FIG. 11 shows the position for the acoustic sensor(s), respiration effort sensor and temperature sensor(s).

In various embodiments, the garment 200 is made of the same material as the textile base for the ECG electrodes. In those embodiments in which the garment 200 includes straps or other connectors, ECG or other electrodes 205 may be placed so as to coincide with the adjustable elastic backings of the straps or other connectors to serve dual purposes, while preserving the overall functionality of the garment 200 (FIG. 10). The connections from the ECG electrodes (FIG. 9(b)) and photoplethysmography device (FIG. 12, inset) are drawn out using fabric-based electrodes made with the same assortment of materials described above. In one embodiment, a garment 200 with a non-standard extended left arm sleeve is provided for accommodating the photoplethysmography band (FIG. 12, inset) and an amplifier-transmitter module with power source 211. The conductive fabric or thread for the conductive fabric- or thread-based connections, which can be made with the same assortment of materials described above, can be stitched on the garment in the form of connective lines that relay the signal from sensors to an onboard amplification-transmission module on a flexible board (e.g. which may be integrated into the control module 300) for seamless integration into the garment 200. The connection scheme can also be optical, which involves enmeshed optical fibers. The gauge of the connective lines is generally a function of the electrical and/or optical ratings of the sensor systems. In various embodiments, the control module 300 can use wireless communication with a remote computing system 400 for data logging and post processing. Given the importance of uninterrupted heart monitoring, the amplifier modules associated with the ECG electrodes of the garment 200 may be equipped to connect to a wired data-logging setup. For example, the amplification circuitry in the amplification modules may include ancillary access points for connecting the respective signal channels to a standard data-logging interface with provisions to one of either a display or a data transmission.

The control module 300 and the remote computing system 400, among other components, are based on standard computer systems having a microprocessor, memory and data storage, input and output, and wired or wireless networking capabilities. The methods and systems described herein may be implemented using one or more such computer systems working in one or more locations to assemble and disseminate data.

The nanostructures 207 of the nanostructured, textile-integrated electrodes 205 (because of their relatively large surface area) are highly sensitive and accurate. Coupled with a low-power microcontroller and Bluetooth module (using one or more of Zigbee, WiFi, and/or other communication protocols as appropriate), the sensor data can be streamed to commercial off-the-shelf cell phones and handheld devices.

In various embodiments the system 20 may include a software application for operation on a smartphone 410 (FIG. 14). The smartphone 410, via the software application, can collect sensor data over Bluetooth or other communications channels and can relay data over 3G, Wi-Fi, WiMax or any outgoing connection using radio-based communications. Using the smartphone 410 and software application, the system 20 does not require any additional custom handheld device for relaying data.

In various embodiments, the software application can provide several additional functions besides basic functions such as data collection and transmission. One possible function is implementation of filtering algorithms on the smartphone 410 to mitigate issues due to motion and other artifacts, rendering cleaner data. In addition, the software application can provide a visualization interface on the smartphone 410 through which users can see salient features of their heart activity such as heart rate. An additional function is that the smartphone 410 software application can tag the data with the location of the wearer of the garment 200. The location (e.g. latitude, longitude) collected is useful for both backend services as well as for the user himself/herself in case of a medical emergency.

In some embodiments, the software application on the smartphone 410 can run machine learning algorithms to perform preliminary anomaly detection. In case of an emergency, it can either alert the wearer and recommend hin1/her to hospital locations near his/her present location or make an automated call to the wearer's physician or emergency personnel with his/her present location. Thus caregivers can access into vital information anywhere and at any time within the healthcare networks for global level active monitoring. As an indication of the scalability of the system, a Zigbee-based WiFi system is capable of handling 65,000 patients at a given time.

In some embodiments the system 20 may include a Global Positioning System (GPS) module, for example as part of the control module 300. Current location data from the GPS module included in the system 20 can be tagged (e. g. by the control module 300 or by the smartphone 410 software application) to the wearer's data and transferred to a remote ("cloud") data cluster and in addition can be stored in a secure database (e. g. an SD card can be installed in the control module 300 to save the data). For physician diagnostics a new backend service may be provided in which the doctor can log into a secured database and visually review the past and current sensor data from the garment 200 system 20 (as necessary). If the physician desires, he/she can employ machine learning algorithms (e.g. embedded in the control module 300, the smartphone 410 software application, and/or the remote computing system 400) to detect abnormalities in the data. Further, a VoIP service can be used to make phone calls or send SMS messages to physicians from the wearer. Additionally, the smartphone 410 or other mobile device can send relevant abnormal data in advance to emergency services in the event the wearer receives medical assistance. The smartphone 410 or other mobile device, if equipped with a camera, can prompt the wearer to start a video call. Processes and steps for emergency or other situations are described in FIGS. 14 and 15.

There are a number of uses of the system 20 disclosed herein, including wireless real-time monitoring of heart rate variability (HRV) and/or ECG and detection of asymptomatic myocardial ischemia in diabetic patients. Real-time monitoring using the system 20 also improves quality of life for patients with medical conditions that can elevate chances of asymptomatic (silent) ischemia attack.

Other uses of the system 20 include monitoring the health of the myocardium after administering ischemia-preventive drugs or reperfusion and disease management for patients with chronic coronary heart disease. The sensors, with wireless signal transmission, present a tool that provides real-time ischemia monitoring for patients while maintaining mobility of the patients.

Software (e.g. the smartphone 410 software application) will give the wearer data such as calories burned during workout, exercise, walking, jogging, and other activities. As noted above, monitoring of data from the garment 200 using a smartphone 410 also permits the use of GPS tracking to identify the user's location. The light weight, comfort, and wireless communications capabilities of the system 20 also allow it to be used for monitoring patients with sleep disorders and for continuous monitoring of stroke patients, ECGs, blood pressure, and any vital parameter of the heart functions in Intensive Care Unit (ICU) in the hospital.

Example 1

The following non-limiting Example discloses a particular embodiment of the wearable remote electrophysiological monitoring system 20.

Initial manifestation of most cardiovascular diseases (CVDs) is usually chest pain or angina. Diagnostic tests are then carried out to decide upon a disease management if not a treatment strategy. At this stage the risk factor for women has been shown to be statistically higher than in men. At age 40 and older, 23% of women compared with 18% of men die within one year after a heart attack. Cardiac related mortalities in women have surpassed mortalities due to all cancers by over 60%. As shown by the plot in FIG. 16, CVD related mortality has been consistently higher in women than in men since 1985.

This difference is also imminent in the case of postoperative survival in women after cardiac surgeries. The reasons cited for such a discrepancy range from increased complexity of cardiothoracic surgeries due to the average small frame and consequently small blood vessel size in women, to the lack of a clear understanding of the influence of menopause related hormonal changes on the autonomic nervous control of cardiac activity and vasovagal balance. The female sex hormone, estrogen, has been known to have a prophylactic effect on the formation and growth of arterial plaques and clots that can stifle the flow of blood through major blood vessels or stop it altogether. This observation has been corroborated by studies on heart rate variability (HRV) indicating the increased involvement of vasovagal balance in young women. However, the administration of estrogen or progestin has been shown to have minimal effect on the outcome of cardiovascular diseases in postmenopausal women. These conflicting findings suggest that the best recourse will be to engage in prognostic measures involving continuous real time monitoring to better track and identify any pathophysiological changes.

Chronic diseases cause subtle changes in the cardiac activity, manifested as irregular heartbeats, aberrational variations in the body's autonomous regulation of blood pressure, and minor transient blockages in flow of blood to the heart referred as ischemic attacks. Chronic diseases such as asymptomatic myocardial ischemia, a decrease in blood supply to the heart, manifest as episodic events that do not leave any diagnostic evidence behind beyond 2-3 min after an episode, making them all the more difficult to identify. These attacks can be detected through variations in the ECG waveform characteristics like the ST segment amplitude and width. Women diagnosed with ischemic heart diseases have a higher frequency of symptomatic episodes as compared with men, which results in more hospitalization and associated costs. Moreover, the variation of T wave amplitude and duration, referred to as T wave *alternans* has been shown to be a predictor of sudden cardiac arrest (SCA) due to ventricular arrhythmias, which is a disease that claims nearly 400,000 individuals every year in the United States. Detection of cardiac arrhythmias or irregular beats from continuous ECG recordings is also an important metric that physicians use for risk stratification and to adjust medication for postmyocardial infarction patients.

Techniques like HRV analysis through time, frequency, and wavelet domain analysis techniques have been successful in tracking autonomic nervous-cardiovascular regulation, which is indicative of chronic diseases as mentioned previously. Thus, various parameters derivable from ECG are of significant prognostic value with regard to CVDs. Sensors that can comprehensively track cardiovascular and pulmonary activity are needed to be able to detect and quantify the electrophysiology of the heart (through ECG), the heart sounds associated with the opening and closing of valves murmur sounds that occur due to inefficient heart valve activity and the activity of the lungs in terms of both the respiratory effort and sounds associated with any blockages or fluid accumulations in the lungs. The full potential of these prognostic tools can be realized only if these sensors can be used. To that end, this paper describes the e-bra, which is used as a platform on which the various sensors for cardiac health monitoring are integrated into the fabric. The end result is an autonomous garment that can collect and transmit vital health signals of the wearer to any desired location in the world through connections to a smartphone and the cellular network or through a Bluetooth enabled PC and the internet. As a first step toward a complete cardiovascular health garment, described herein are means for acquiring ECG signals from a subject using the e-bra, transmitting the data to a smartphone or a Bluetooth enabled PC and perform the above mentioned power spectrum analysis of the HRV.

The use of a smartphone as a base station for receiving data offers the advantage of cellular network connectivity to the Internet and consequently, the availability of cloud computing resources for real time automatic anomaly detection and response to critical emergencies. To address this capability, disclosed herein is a protocol for response to emergencies from both the cloud backend and the smartphone.

The electrocardiogram (ECG) is a simple noninvasive diagnostic test performed to observe any abnormalities in cardiac electrophysiology. The ECG waveform acquired from a derived Lead II electrode placement system is shown in FIG. 17(a), which clearly depicts the classical components of the ECG waveform (FIG. 17(b)). The waveform characteristics of the ECG include P wave, QRS complex, and T and U waves (FIG. 17(b)).

PR interval, QRS duration, ST segment duration, T wave amplitude (referred as T wave alternate), and T wave width are the diagnostically relevant quantities obtained directly from the data. The derived quantities of interest are R peak to R peak interval (for heart rate determination and arrhythmic cardiac activity detection), variability in ST segment duration and amplitude, and power spectrum and wavelet domain analysis of HRV sequences obtained from the RR interval (RRI).

The 12 lead ECG including three augmented limb leads, three limb leads, and six chest leads gives a comprehensive observation of the electrophysiology of the heart from all angles. However, the continuous monitoring of all 12 lead ECG is only required for high risk patients who have already been diagnosed with CVD. Moreover, the use of a full 12 lead system for everyday monitoring can be inconvenient and cumbersome. An alternative five electrode system that gives all the diagnostic information of a 12 lead system can be used for continuous monitoring instead. FIG. 9(a) shows the lead placements for the 12 lead system and FIG. 9(b) shows the similar implementation on the e-bra with textiles or gold nanowire electrodes, where the nanowires may be shaped as one-dimensional (wires) and/or three-dimensional (helices) nano structures.

The RRI is the time elapsed between the onset of an R peak of the ECG and that of the next and hence signifies the time between two consecutive beats. The variability of this interval is referred to as HRV. It is well known that the human RRI series has three major frequency components: (i) the very low frequency (VLF), (ii) the low frequency (LF), around 0.1 Hz, and (iii) the high frequency (HF), between 0.2 Hz and 0.4 Hz. Consequently, algorithms for extracting the RRI involve an identification of the instances of the R-wave occurrence or of the QRS complex in the ECG data, followed by concatenating the time-differences between successive instances. The RRI series is rich in information about the cardiovascular physiology of a subject.

Although there is some disagreement with respect to the physiological indication of the LF component, most studies consider LF to be an indicator of sympathetic nerve modulation of heart rate. The HF reflects vagal nerve influence on the same. The ratio LF/HF is used as a diagnostic quantity that can reflect the autonomic neuropathy due to chronic diseases such as diabetes. A reduction in this ratio has also been observed in the case of postmyocardial infarction patients. A lower HRV has been shown to be indicative of compromised cardiac health. Thus HRV analysis has been studied as a valuable, noninvasive and easy to implement diagnostic tool. However, it is important to note that factors such as fiducial point selection for HRV calculation, sampling rate, and considerations of data latency are key to obtaining reproducible results. The inclusion of HRV analysis of supine and head-up tilt ECG of a subject acquired through the e-bra validates both the e-bra and the acquisition system as reliable cardiac health monitoring system.

Figure 18:
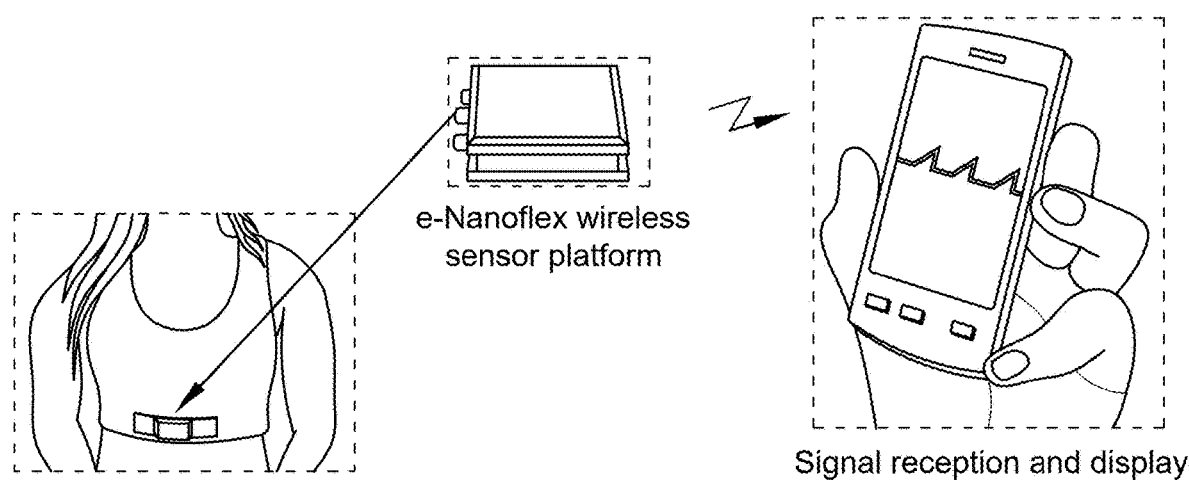
FIG. 18 shows an e-bra worn by a test subject, the control module, and the smartphone display interface.

Recent developments in embedded computing and the emergence of smartphones as powerful portable computing devices have made truly pervasive computing a reality. Along with significant computing power, the communication protocols for interdevice communications have also become more reliable and offer high data rates of the order of 3 Mbit/s, e. g. as seen with Bluetooth™ version 2.1. The various sensors disclosed herein are incorporated in the e-bra and the signals from the sensors are brought to the control module through conductive threads, which are made from silver-coated fabric. FIG. 18 shows a picture of the e-bra, the control module used for data acquisition and wireless transmission, and a smartphone display interface for an application that plots the data received from the control module.

Figures 13A, 13B, 13C:
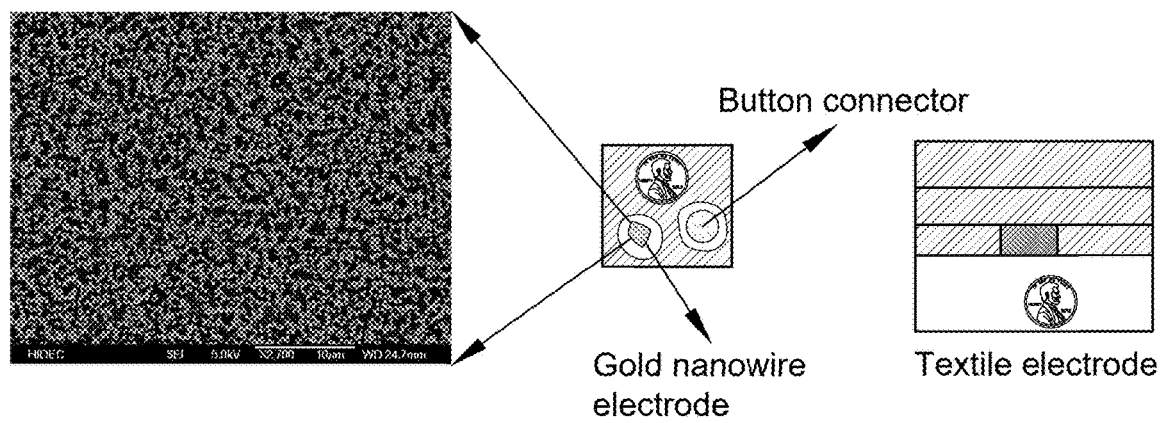
FIG. 13(a) shows a scanning electron image of gold nanowires such as those used in embodiments of the nanostructure-based electrodes.
FIG. 13(b) shows gold nanostructure-containing electrodes mounted on a standard snap-on button.
FIG. 13(c) shows conductive fabric incorporating a textile electrode which includes nano structures.

ECG measurements are due to the change in impedance across the heart measured at the level of the skin. It is an information rich signal that is regularly used to diagnose various kinds of cardiac ailments. In this Example, ECG data has been acquired from two subjects with the e-bra, which is a textile based platform with the electrodes mounted on it. Commercially available electrodes for ECG use Ag/AgCl electrodes with a conductive gel that minimizes the impedance between the skin and the electrode. Due to problems of gel drying that results in noise signals and strong adhesives, it causes discomfort when worn for long durations. Dry electrodes offer a much more comfortable and durable alternative. To this end, if a garment needs to be able to pick up good quality ECG and has to be worn every day and throughout the day, it needs to use dry and washable electrodes such as the gold nanowire electrodes or conductive fabric based electrodes that can be easily stitched onto the e-bra. FIGS. 13(*a*)-13(*c*) show the gold nanowire electrodes and the conductive fabric electrodes that are used to acquire ECG from the subjects.

In experiments, two electrodes were placed in the positions described as V1 and V2. The difference in potential between these two positions is known to show a distinct and sharp peak in the signal that corresponds to the activation of the left ventricle of the heart, namely, the R peak of the ECG. The left ventricle of the heart pumps blood from the heart to the peripheral arteries and is used as an indicator that corresponds to the completion of one cardiac cycle. The signal also shows Q, S, and T waveforms, where S-T segment is for ventricular repolarization.

A three stage differential amplifier was used with a maximum gain of 65 dB and a 3 dB bandwidth of 0.1-70 Hz. The amplified output signal of the amplifier was digitized by an Atmega 328P microcontroller (Atmel Corporation, San Jose, Calif.) at 200 Hz and transmitted through a Bluetooth module (STMicroelectronics, Geneva, Switzerland).

Figure 19A:
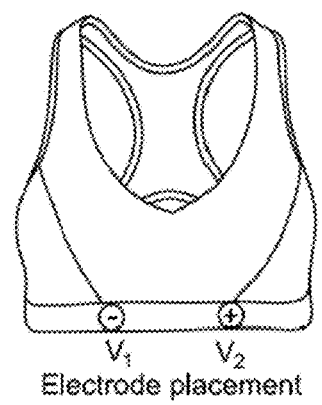
FIG. 19(a) shows the electrode positions on the e-bra.
Figure 19B:
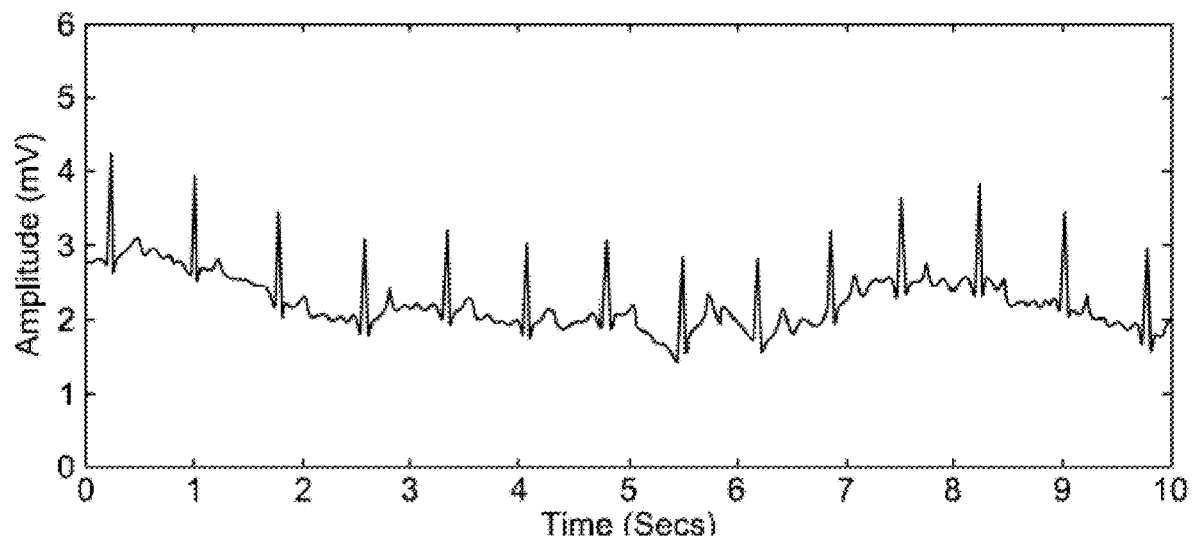
FIG. 19(b) shows data acquired from subject 1.
Figure 19C:
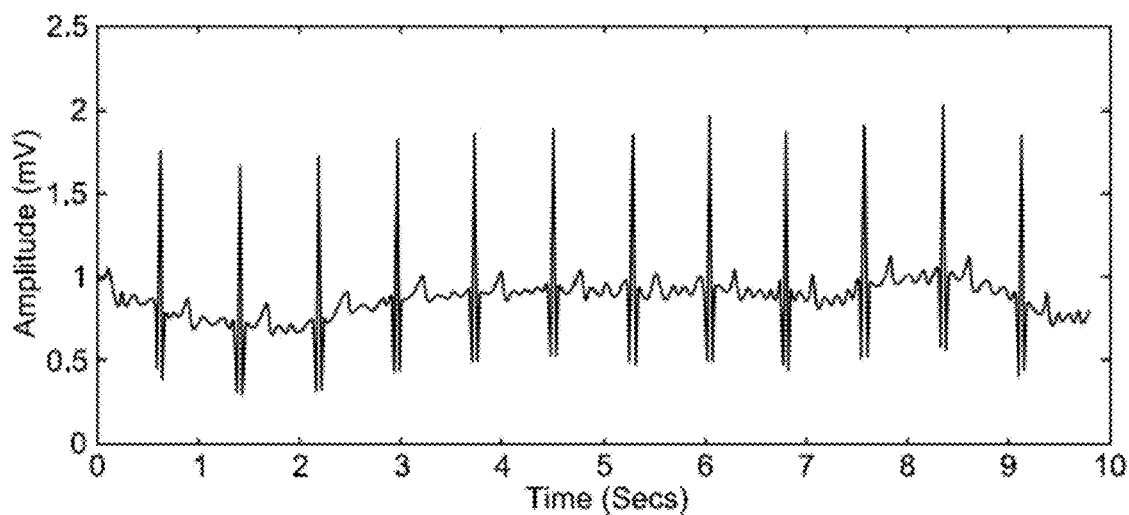
FIG. 19(c) shows data acquired from subject 2.

The signal conditioning algorithms, the R peak detection algorithms, and the HRV analysis were implemented on a PC. Data were acquired from two healthy subjects and the data acquired are plotted in FIGS. 19(*b*) and 19(*c*).

Figure 20:
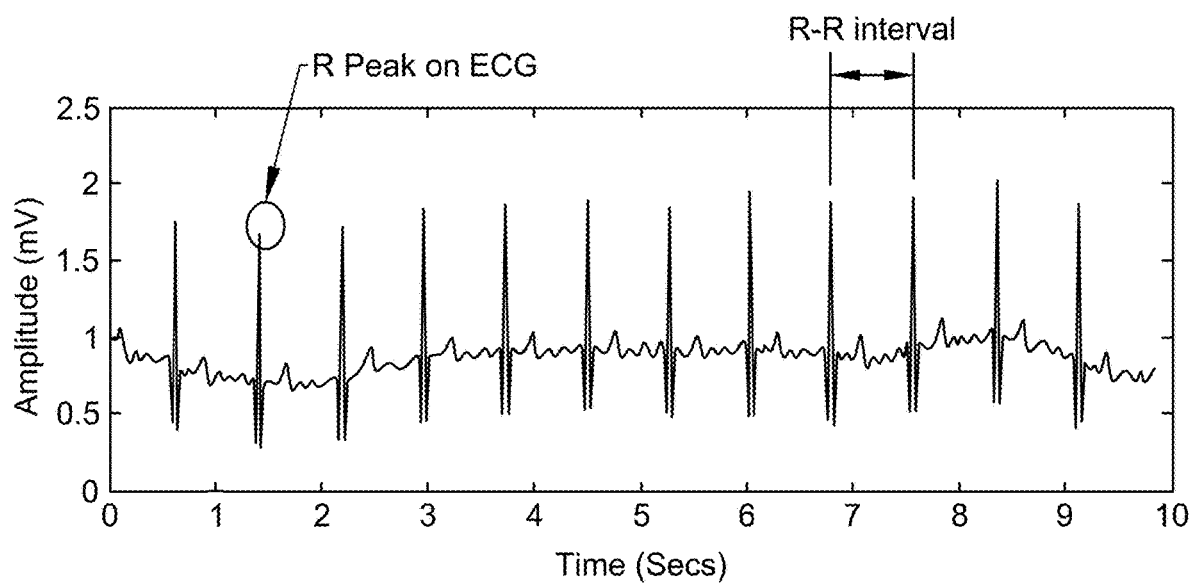
FIG. 20 shows R-R interval determination from an ECG.

As discussed above, heart rate variability has received great interest as a prognostic and diagnostic tool over the past two decades. Heart rate variability is described as the sequence formed by concatenating the difference in heart rate between consecutive beats. The inverse of this quantity is the difference in the intervals between consecutive R peaks. By detecting the R peaks, the interval between them can be identified and hence obtain the heart rate variability signal against beats, as shown in FIG. 20. A robust R peak detection algorithm was implemented along with a subroutine for calculation of RRI and derivation of HRV.

Figure 21A:
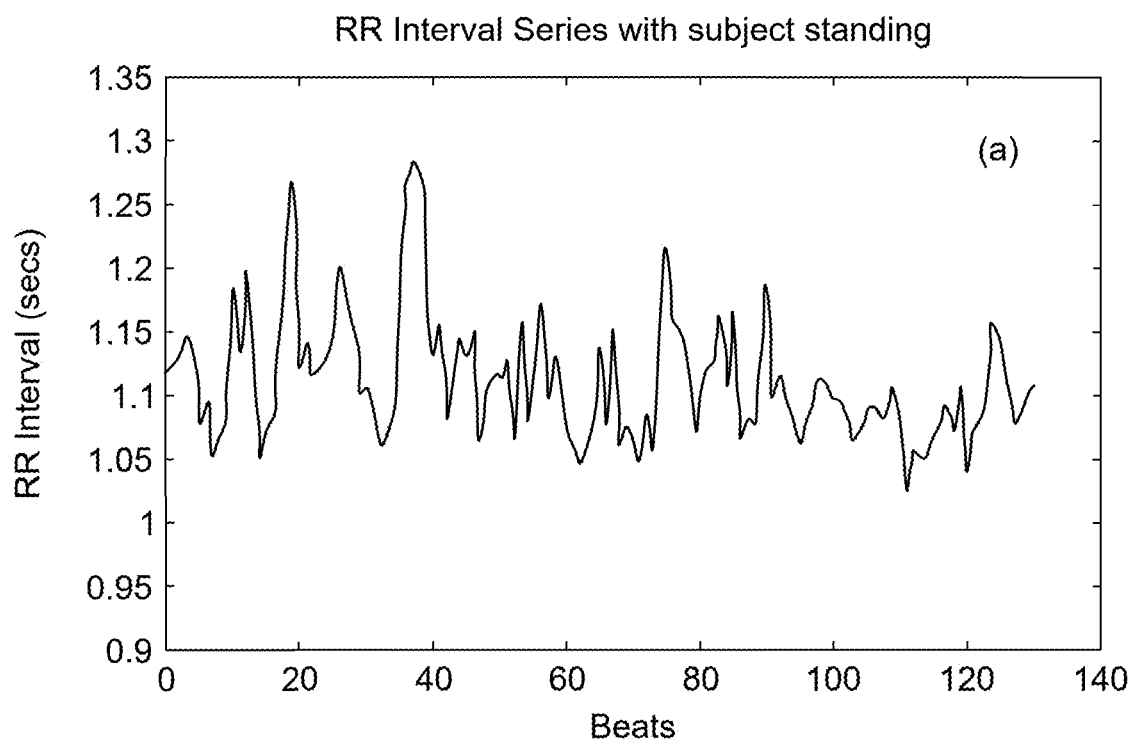
FIG. 21(a) shows a plot of the RR interval series against beat number.
Figure 21B:
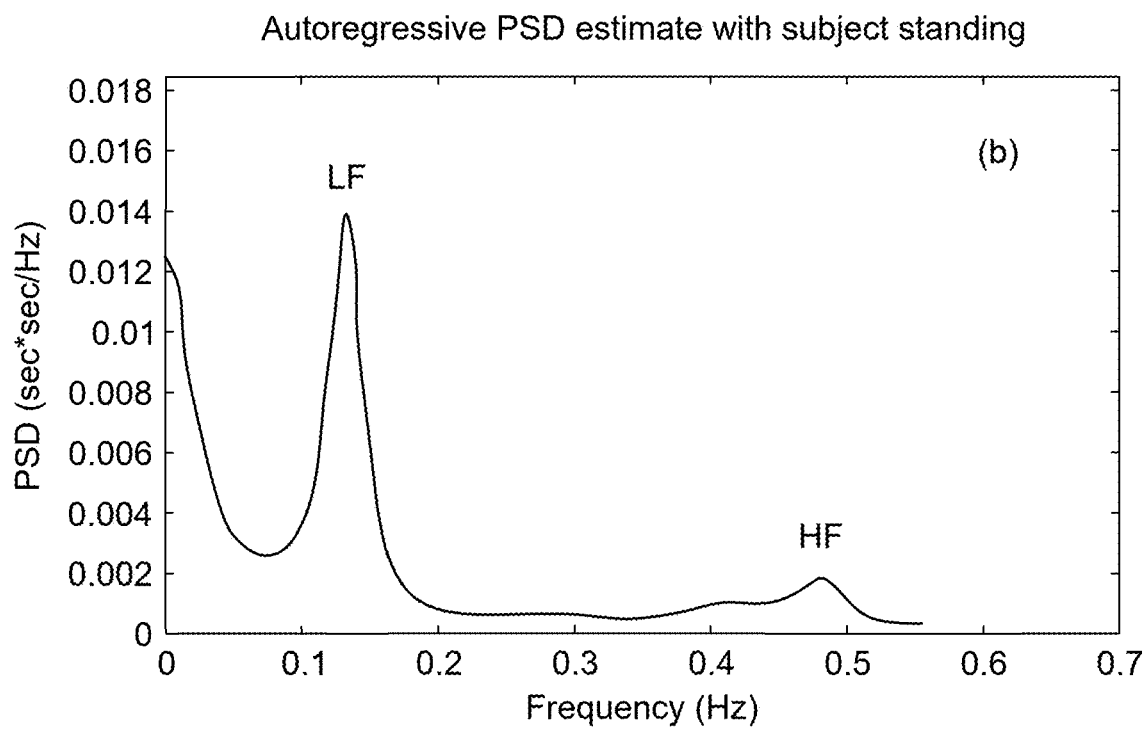
FIG. 21(b) shows a plot of the AR PSD computed from the RRI series for the standing case.
Figure 22A:
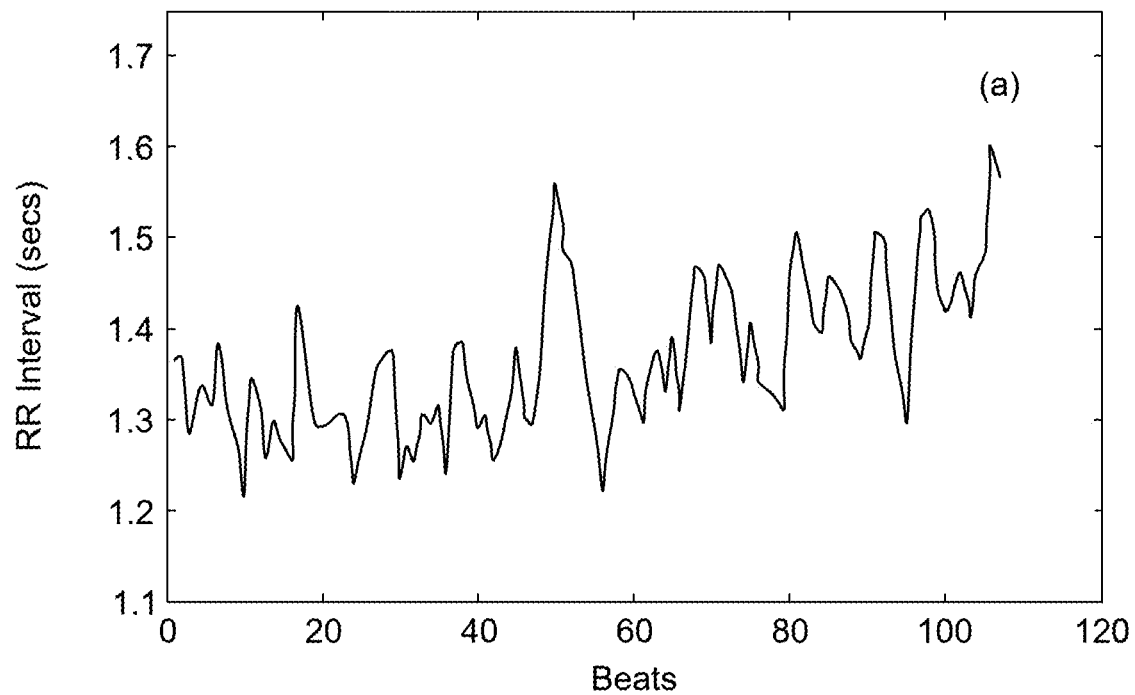
FIG. 22(a) shows a plot of the RR interval series against beat number.
Figure 22B:
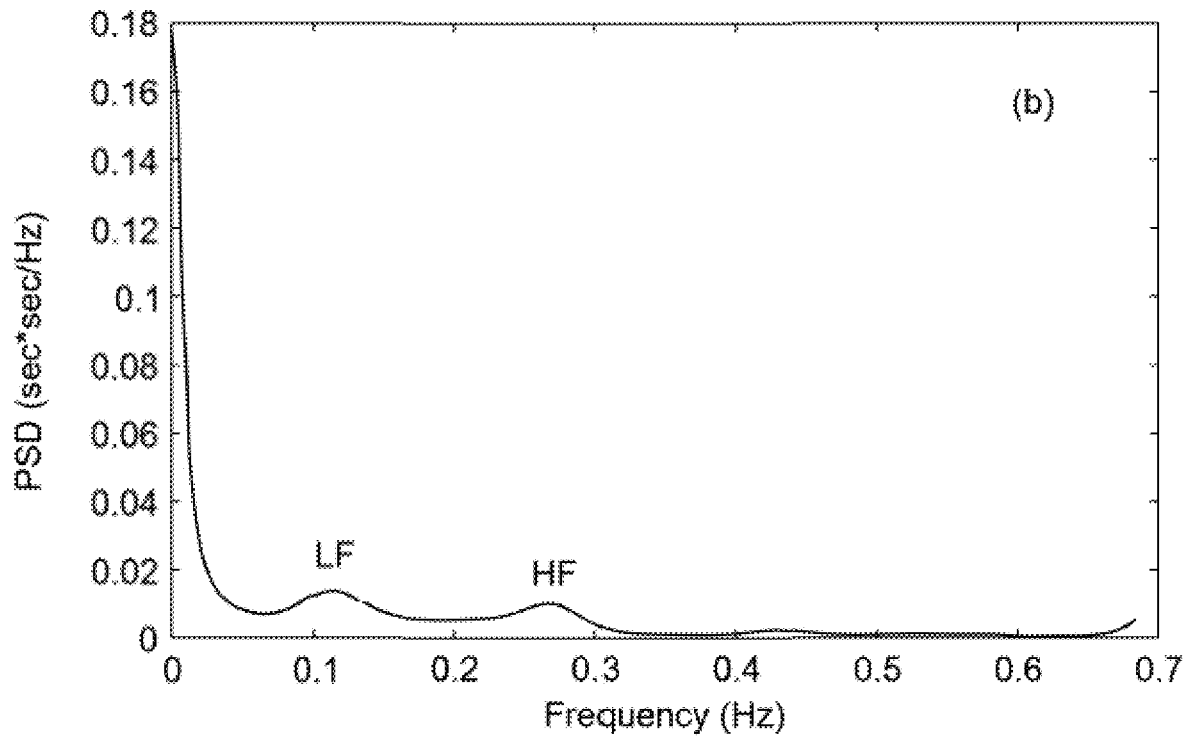
FIG. 22(b) shows a plot of the AR PSD computed from the RRI series for the standing case.

The autoregressive (AR) power spectrum estimation technique was used to obtain the power spectrum density (PSD) plot with the characteristic LF and HF peaks. The AR PSD is best suited for short data record lengths and performs very well as a frequency estimator for signals with strong sinusoidal components such as the HRV signals. A 150 s record of ECG was collected for a normal healthy female of age 18 in supine position and while standing still. The support of the RR interval signal is beats and the sampling frequency used for AR PSD computation was chosen to be the mean RR interval. FIG. 21(*a*) shows the plot of the RR interval series plotted against beats and FIG. 21(*b*) shows the AR PSD computed from the RRI series for the head-up tilt case. FIGS. 22(*a*) and 22(*b*) show the same for supine ECG. In the case of head-up tilt, the heart rate was higher as compared with the supine ECG. The classic shift in the power distribution between low-frequency (LF) and high-frequency (HF) components with respect to the total power in each case is evident from the AR PSDs in FIGS. 21(*b*) and 21(*b*). Thus, the implementation of an e-bra for cardiac monitoring is shown to be a reliable system for tracking of chronic conditions related to autonomous nervous regulation of cardiac activity.

As mentioned above, complete cardiac monitoring will require real time ECG for the detection of arrhythmic heart beats, ST segment abnormalities associated with ischemic attacks, myocardial infarction, and other waveform characteristics such as PR interval and QRS complex width. These are indicative of the functioning of the atria of the heart and blockages in the cardiac electric conduction pathways, respectively. HRV analysis, on the other hand, provides insight into changes in the regulation of cardiovascular function stemming from chronic diseases such as diabetes and hypertension, which are major risk factors for the occurrence of CVDs.

Figure 23:
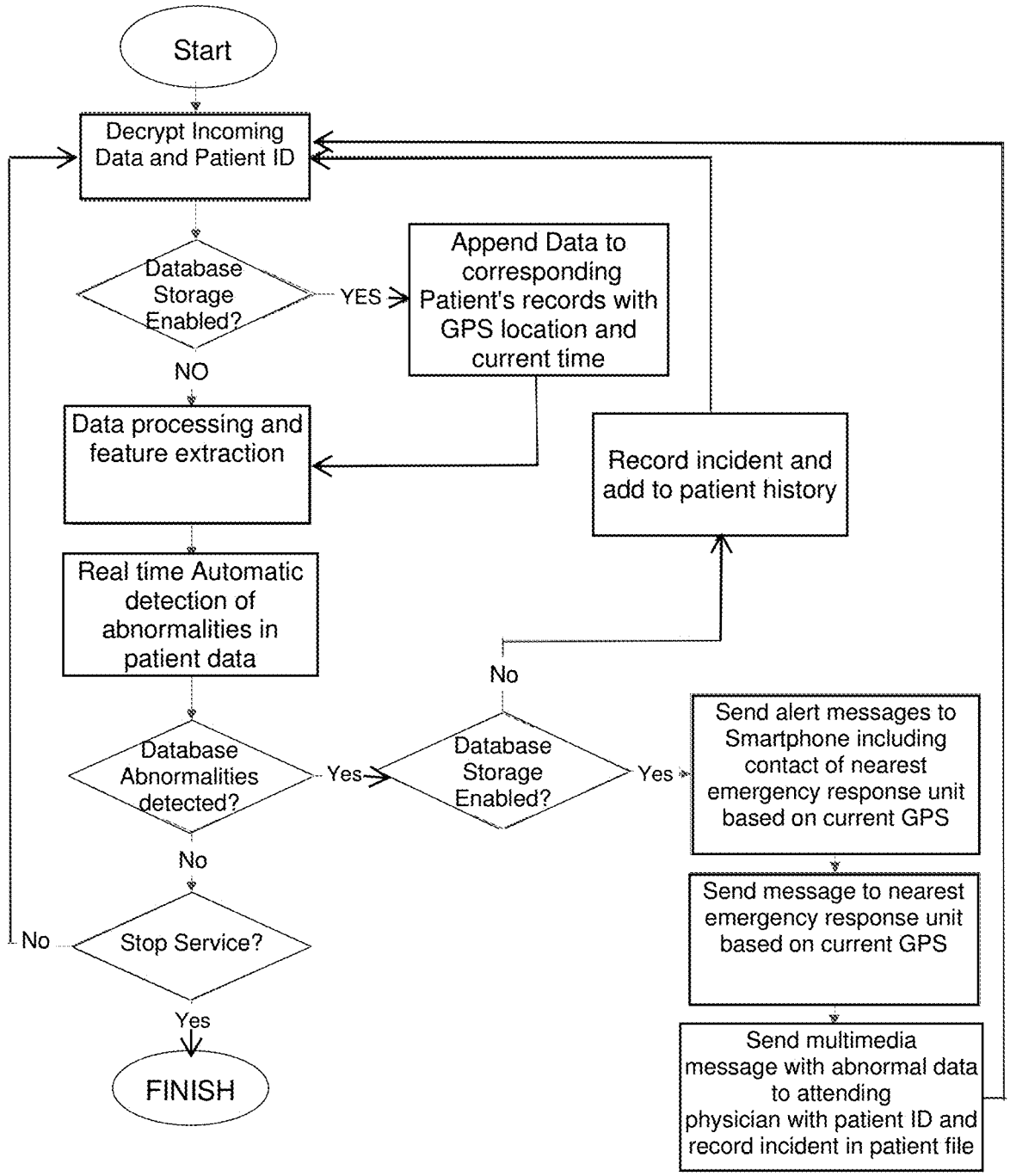
FIG. 23 shows the sequence of processes and steps followed by the cloud server when an emergency abnormal condition reflected by abnormal health data is detected.
Figure 24:
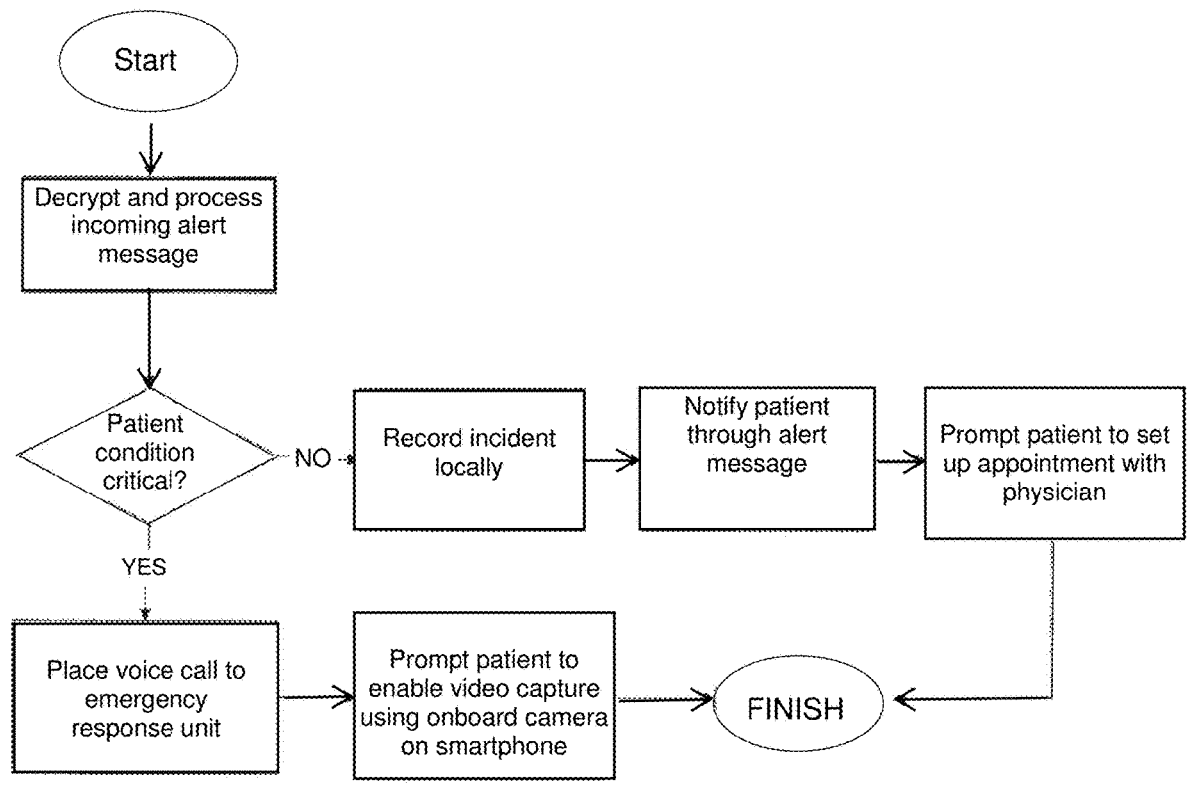
FIG. 24 shows the sequence of processes and steps followed on the mobile device in response to an emergency message sent by the cloud server.

The tracking and assessment of long-term chronic diseases through techniques such as HRV analysis alone does not realize the full potential of the e-bra system. The incorporation of additional intelligence into the system to automate and facilitate quickest possible response to any emergency situation is vital to realize the full potential of this system. Taking this requirement into consideration, the system disclosed herein can harness the computing power of the cloud cluster through the connectivity of the smartphone to the Internet, e.g. through the cellular network. Also proposed is a protocol for the response from a backend server in the event of such an emergency and a concomitant protocol for alerting the wearer through the smartphone. The overall system includes the wearer's Smartphone, a device on the Emergency Medical Service (EMS) vehicle that responds to the emergency, the attending physician's Smartphone, and the wearer's physician. The flow chart in FIG. 23 describes the response at the backend server.

At the Smartphone end, there are a number of standard utilities that can be used in case of an emergency such as the onboard video camera, Voice over Internet Protocol (VoIP) connectivity, and Global Positioning System (GPS). The flow chart in FIG. 16 shows the proposed response protocol at the wearer's Smartphone. The video capture option is included here so that EMS personnel may be able to provide instructions to the wearer as appropriate for the circumstances.

This non-limiting Example describes an embodiment the e-bra platform for the mounting of heart monitoring sensors and the incorporation of wireless communication to this platform. Heart rate variability analysis has been performed based on the data acquired from a subject with the e-bra and it has been shown that the e-bra can be used as a reliable means of assessing chronic cardiac conditions in patients including women. There are a number of advantages of using an automated abnormality detection scheme and a protocol is proposed which can be followed for the response to an emergency from the backend server, the Emergency Medical Service vehicle, the attending physician's phone, and/or the wearer's smartphone.

Example 2

Vigorous exercise and exertion is known to increase the risk of Sudden Cardiac Death (SCD) in individuals with underlying cardiovascular diseases (CVD). Recently, SCDs have been reported with a high rate of occurrence among athletes in soccer, football and basketball. Prescreening athletes with 12-lead Electrocardiograms (ECG) has been a successful measure to identify individuals at high risk for SCDs and exclude them from participation. The total cost for such prescreening of athletes is estimated to be in the order of $10B/year. The high risk of SCDs during training or exertion suggests that ECGs are of far greater value when acquired real-time during the actual training where abnormal cardiac electrophysiology can be tracked and identified before the onset of symptoms. The availability of such immediate diagnostic data will also significantly reduce the time taken to administer the appropriate resuscitation shock. This Example discloses an embodiment of a wearable remote electrophysiological monitoring system which includes a fully wearable textile integrated real-time ECG acquisition system with wireless transmission of data for the continuous monitoring of football players during training and on the field during games. The system is applicable also to basketball players, soccer players and other athletes, as well as members of high-stress occupations such as military personnel, police, firefighters, and various other emergency responders.

This Example uses the specific case of football players as an example to illustrate the invention because of the high incidence of SCDs in football players in the United States. While specific references may be made in the Example to football players and their equipment, it is to be understood that the basic principles of this Example are equally applicable to other high-stress occupations such as those listed above.

Important factors to be considered in the implementation of this wireless cardiac monitoring systems include the accuracy and reliability of signals that are acquired along with an unobtrusive design. The system uses dry textile sensors and nanocomposite printed connection traces made with conductive nanoparticles, on a base layer compression vest to acquire ECG signals. These signals are then amplified and transmitted wirelessly using ZigBee, Wi-Fi, GSM and others on a compact module that could be placed in a pocket within the athlete's protective shoulder pad.

Figure 25:
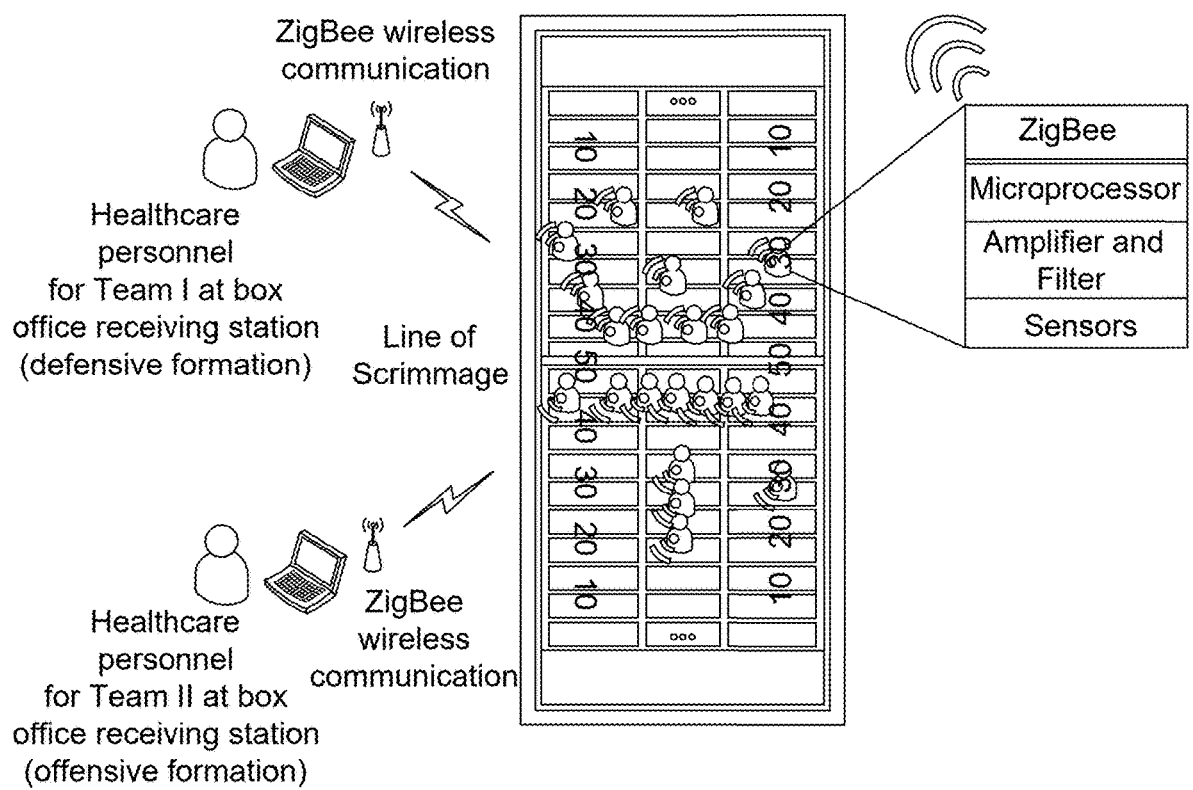
FIG. 25 shows a schematic of the overall implementation of the football player monitoring system.
Figure 26A:
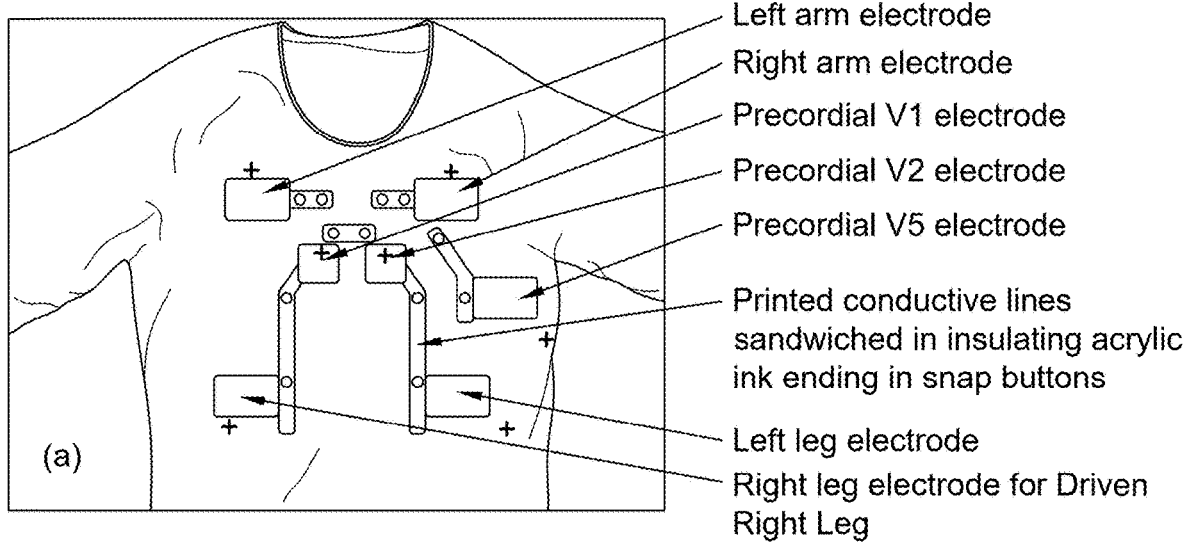
FIG. 26(a) shows a compression base layer garment with sensor electrodes and printed traces.
Figure 26B:
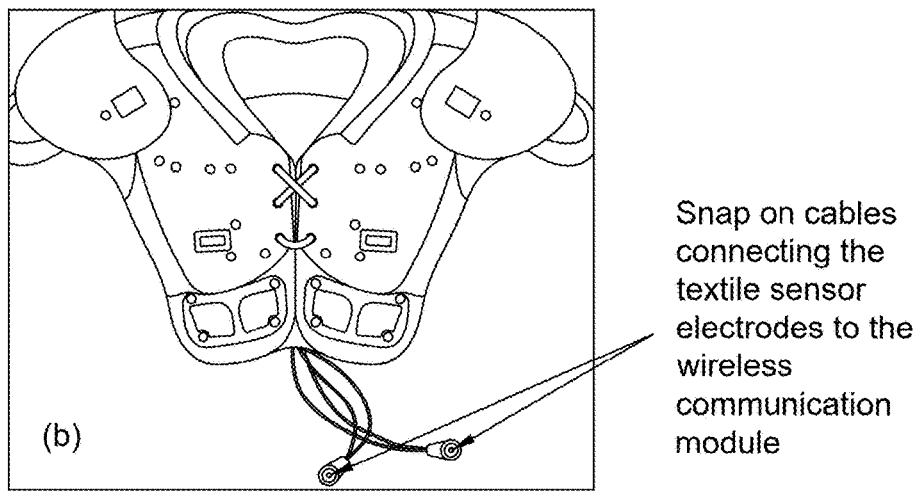
FIG. 26(b) shows protective shoulder pads with snap on connection cables to connect sensors to a wireless module.
Figure 26C:
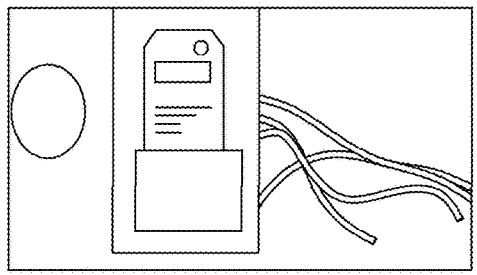
FIG. 26(c) shows a wireless module with a 5-channel amplifier and an XBee ZigBee module.
Figure 26D:
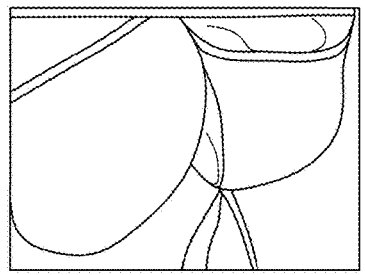
FIG. 26(d) shows a wireless communication module placed in a pocket on the interior of the shoulder pad.

In general, the system for cardiac monitoring disclosed herein, which incorporates embodiments of the wearable remote electrophysiological monitoring system disclosed above, may be deployed in areas where high-stress activities are taking place, such as sporting events, combat zones, or emergency scenes, and is suitable for use in non-clinical settings where the high-stress activities are actually taking place. As shown in FIG. 25, one or more wireless monitoring stations is located in the area where the activity is taking place and one or more participants wears a monitoring system as disclosed herein. In some cases (e.g. sports teams), there can be separate monitoring stations for subgroups of participants in order to maintain privacy of the data. The type of wireless communications technology that is employed, along with considerations such as local signal interferences (e. g. buildings, topography, nearby interfering radio sources) will determine the area or radius from which signals can be acquired and how many wireless receivers need to be deployed. In the embodiment disclosed herein, the ZigBee wireless system that is used has a range of up to 1 mile.

The sudden death of an individual resulting from a sudden failure in heart function is referred to as Sudden Cardiac Death (SCD). Vigorous exercise increases the risk of SCDs in young athletes with underlying cardiovascular disorders (CVD). A recent study has shown that up to 82% of individuals who succumbed to SCD were engaged in strenuous exercise during or immediately before the incident. Nearly 58% of SCDs reported between 1980 and 2006 have been reported in basketball and football athletes. Recent studies have shown that the incidence of SCDs in young athletes in the US at the high school and college level have been underestimated in previous studies. All of the data available thus far on SCDs have been through retrospective studies involving news reports, internet databases and subjective accounts. Albeit illuminating, it is important to note that these studies are inevitably under representative of the real scale of the problem.

The most prevalent causes of SCD in young athletes are CVDs and sports related injuries. Among CVD causes, the most prevalent are Hypertrophic Cardiomyopathy (HCM) (36% of cases) and coronary artery diseases (CAD) (17% of cases). Among sport injuries, Commotio Cordis and blunt trauma injuries together account for 25% of all SCDs recorded between 1985 and 2006. The current strategy for the prevention of SCDs in young athletes is to prescreen them and diagnose any cardiovascular diseases that may put them at high risk for SCDs, and promptly disqualify them from participation if diagnosed. The proven approach implemented in Italy has involved a mandatory prescreening with detailed history, physical examination and a 12-lead ECG with guidelines and criterion for identification of cardiovascular abnormalities that may put the athlete at high risk for SCD. The American Heart Association (AHA), however, does not currently recommend the inclusion of 12-lead ECG as a part of the prescreening for several reasons: the high direct costs of the tests, the lack of dedicated trained athletics personnel to perform the prescreening in place of physicians, the sheer number of athletes to be screened and reported low specificity, and high rates of false positives and false negatives of ECG interpretations. Although the positive diagnostic value of including a 12-lead ECG to the prescreening has been identified by both the European society of Cardiology (ESC) and the AHA consensus panels for recommendations on cardiovascular screening of young athletes, the cost-effectiveness of including a 12-lead ECG to the US athletic prescreening protocol is still a subject of wide debate.

Despite the evidence suggesting the effectiveness and initial success of the prescreening with ECG in Italy, there are four limitations to the prescreening approach that need to be addressed:

First—There is still wide debate on the differential diagnosis of HCM from the ECG changes brought on by training in many athletes with otherwise normal hearts (athlete's heart). Reported differences in training induced cardiac remodeling between athletes of African origin and others have made diagnosis based on ECG findings equivocal. Moreover, the remaining two prevalent causes for SCD (CADs and blunt trauma injuries) cannot be diagnosed during prescreening as CADs do not manifest as ECG abnormalities and blunt trauma injuries are non-pathological and can occur to any athlete with an otherwise healthy heart.

Second—Recommendations suggest that for differentiation of HCM from athlete's heart, Brugada-like ECG abnormalities, arrythmogenic right ventricular cardiomyopathy or dysplasia and features like prolonged PR intervals, short PR intervals, early repolarization and inverted or biphasic T waves can be further evaluated using an exercise test to improve specificity. However, this is to be done in addition to the preliminary ECG screening at an added cost.

Third—From the perspective of secondary prevention i.e. through the adoption of strict guidelines on Sudden Cardiac Arrest (SCA) resuscitation, it is imperative that an SCA is promptly recognized, cardiopulmonary resuscitation (CPR) is started immediately and a defibrillating shock is applied as soon as possible. The target resuscitation time recommended by the AHA is between 3-5 minutes, from the time the athlete's collapse was witnessed to the application of the defibrillating shock. It has been shown that survival chances may drop by 7-10% for every minute that defibrillation is delayed. In the absence of a real-time ECG, the emergency responder or rescuer has to first identify an SCA with accurate pulse or respiration assessments while the athlete may be gasping or having myoclonic jerks or seizure-like activity that may be inconsistent with an SCA.

Fourth—The various mechanisms for SCD have been studied extensively at the cellular process and ionic channels level. This work needs to be augmented with real-time studies on the mechanism of SCD using non-invasive techniques like ECG, which are lacking. The ECG is rarely or never available during a sudden cardiac arrest episode. Therefore, a system for real-time monitoring of cardiac electrophysiology during exertion, which put the athletes at higher risk of SCDs, is an important step in the prevention and treatment of sudden cardiac arrest in athletes.

In this invention, we have developed and evaluated a fully wearable real-time ECG acquisition system with wireless transmission of data for the continuous monitoring of football players during training and on the field. We have chosen the case for football players because of the high incidence of SCDs in football players. Moreover, the protective gear worn by football players offers several design options for both the concealment and protection of the electronic components, so as to not hinder the performance of the player in any way. Dry textile sensor electrodes (such as the nanostructured, textile-integrated electrodes discussed above) are stitched into the football player's base layer compression vest. The electrodes may be integrated into the fabric of the garment or pieces of a second fabric containing the electrodes may be attached to suitable locations on the garment, e.g. by sewing or adhesive. Conductive inks are used to draw traces from the electrodes which are then connected to the amplifier and wireless transmission module embedded in the player's shoulder pad.

The system design was formulated to optimally satisfy three criteria.

First, the quality of signals acquired. This determines the choice of sensor electrodes for ECG, printed traces on the athletic base layer compression vest that connect the sensors to the wireless communication module and the hardware design for signal amplification and filtering for noise removal.

Second, the functionality of the system, in terms of modalities of signals acquired. This addresses a trade-off between maximizing the number of sensors required to acquire all of the diagnostically important vital biomedical signals, and maintaining signal accuracy and the overall usability of the system in a manner that does not interfere with the athlete's performance. In a conventional hospital setup for 12-lead ECG measurements, the Ag/AgCl electrodes can be placed at precise locations specific to the patient's anatomy. However, with garments being flexible and elastic, it is not practical to expect the same level of reproducibility as a clinical ECG in terms of electrode positioning. Therefore, in this paper we have used a reduced set of the 12-lead ECG, namely, leads I, II, V1 and V5-V6. This reduced set of leads was chosen based on the recommendations in Uberoi et al. (Circulation, 2011; 124:746-757), summarized in Table 1. An electrode is placed at the V1 position to gain perspective of the left atrium activity, at the V2 position to gain perspective of the right atrium activity, and an electrode spanning the V5-V6 positions for ventricular activity. A full frontal ECG consisting of the Limb leads and the augmented limb leads (aVF, aVR and aVL) can be algebraically derived if any two pairs among Lead I, II and III signals are known. The full frontal ECG is required to determine the QRS axis deviation.

Third, the Quality of Service (QoS) offered by the wireless communication module. This determines the extent of sensor data (in this case, ECG) loss during transmission from the football player to the receiving station due to intermittent wireless connection loss. This type of sensor data loss manifests as abnormal ECG waveforms when the actual athlete's heart function might be normal. These incidences, if not identified and either excluded or corrected, will lead to false positive diagnoses. Therefore, it is important to maintain good QoS within the range of the football field for all players. The system has to ensure continuous connectivity and availability of diagnostic data from all eleven players on the field at all times.

TABLE 1

| ECG wave feature | ECG leads of interest | Criteria according to ESC [16] | Criteria according to Uberoi et al [13] |
| --- | --- | --- | --- |
| Q waves | I, II, III, aVF, aVL, V5, V6 | >4 mm depth (0.4 mV) below isoelectric | >3 mm depth (0.3 mV below isoelectric) and/or >40 ms in aVR, III, V1 |
| ST Depression | I, aVL, V5, V6 | Further evaluation for any ST depression | >0.5 mm (0.5 mV) below isoelectric between J-junction and T-wave onset >1 mm in any lead |
| T wave inversion | I, II, III, aVF, aVL, V2, V3, V4, V5, V6 | Further evaluations for >2 mm (0.2 mV) inversion. I, II, III, aVF, aVL, V5, V6 | >1 mm (0.1 mV) in I, II, aVF, aVL, V3-V6 non-African origin athletes. In athletes of African origin, inversion without ST elevation in leads of interest. |
| Atrial abnormalities | II, V1, V2 | Same as Uberoi et al [13] | V1, V2-negative portion of P was <40 ms and 1 mm (0.1 mV) depth, total P wave duration >120 ms II-P wave amplitude >2.5 mm |
| Right Ventricular Hypertrophy | I, II, III, aVF, aVL, V2, V3, V4, V5, V6 | Same as Uberoi et al [13] | >30 years, then V1-R wave greater than 7 mm (0.7 mV), R/S ratio >1 V1, V5, V6 - sum of R wage in V1 and S wave in V5 or V6 >10.5 mm (1.05 mV) <30 years, right atrial enlargement, V2, V3 - |

TABLE 1-continued

| ECG wave feature | ECG leads of interest | Criteria according to ESC [16] | Criteria according to Uberoi et al [13] |
| --- | --- | --- | --- |
| Left Bundle Branch Block (LBBB), Right Bundle Branch Block (RBBB), Intraventricular Conduction Delay (IVCD) | I, II, III, aVR, aVF, aVL, V1, V2, V3, V4, V5, V6 | Same as Uberoi et al [13] | T wave inversion or II - right axis deviation >115° QRS >120 ms |
| QRS axis deviation | I, II, III, aVR, aVF, aVL | Not specified | Leftward <−30°, Rightward >115° |
| QTc interval | II, V5 | Any athlete >380 ms or >500 ms, Males 440 ms-500 ms, Females 460 ms-500 ms | Males >470 ms, Females >480 ms, Any athlete <340 ms |
| Brugada pattern | V1, V2 | Downsloping ST-segment with a $ST_J/ST_{80}$ ratio >1 | Coved ST segment gradually descending into an inverted T wave |
| Pre-Excitation | II | Same as Uberoi et al [13] | Delta Waves and PR interval <120 ms |
| Ventricular extrasystoles, heart block, and supraventricular arryhthmia | I, II, V1, V2 | Not specified | Atrial fibrillation/flutter, supraventricular tachycardia >1 premature ventricular contraction in a single 12-lead recording. |

The schematic in FIG. 25 shows the desired overall system implementation for the monitoring of football players on a football field.

The system consists of three components: (1) The sensor platform which is the base layer compression vest with the electrode sensors and the printed connection traces worn by all football players. (2) The Wireless module that consists of the amplifier and signal conditioning circuits, a microcontroller and the ZigBee wireless radio. (3) The software at the receiving station that plots the incoming data from the football players.

Sensor Platform

The wearable ECG platform includes a garment that was fabricated as a vest with dry textile-based electrodes. The garment may be an undershirt (e.g. an UNDERARMOR® shirt), bra (e.g. a sports bra), or other undergarment of which at least a part is in contact with the wearer's skin and which is sufficiently stretchable and/or tight-fitting so as to promote contact of the electrodes with the wearer's skin. Conductive tracks were printed on the vest fabric to electrically couple the ECG electrodes to a centralized amplification and transmission electronics. The inks for conductive tracks were formulated with silver nanoparticles and elastic acrylic based binder to obtain a flexible nanocomposite trace compatible with the fabric. The ink formulation was printed onto the fabric using screen printing technology. In some embodiments wires such as copper wires may be used for electrically coupling the electrodes to the controller instead of, or in addition to, conductive (e.g. silver-based) materials that are applied to fabric. In various embodiments, the electrical coupling material is compatible with cleaning of the garment and/or is removable during cleaning.

In various embodiments, the processing of signals from the electrodes may be carried out in a number of ways, for example with most or all of the ECG calculations being performed by the controller of the wearable platform. In other embodiments, the electrode signals may be transmitted (e.g. after being digitized) to a receiving station where they are processed by the controller associated with the receiving station to produce an ECG. In still other embodiments, the wearable platform controller may perform initial calculations to produce an ECG and also transmit raw electrode data to the receiving station for additional processing and for archival purposes. In still further embodiments, the receiving station may transmit data onto a network for processing, analysis, and archiving at a remote location(s).

The transmission electronics were housed in the protective shoulder pads worn by them athlete over the vest. The connections between the amplification-transmission electronics and the conductive traces were made with metalized snap buttons, although other types of removable electrical connections are also possible. By design, the snap button allows the athlete to make connections after putting on the shoulder pad. FIG. 26 shows the actual base layer vest used for testing and the wireless communication module mounting on the shoulder pad.

Wireless Module

Figure 27:
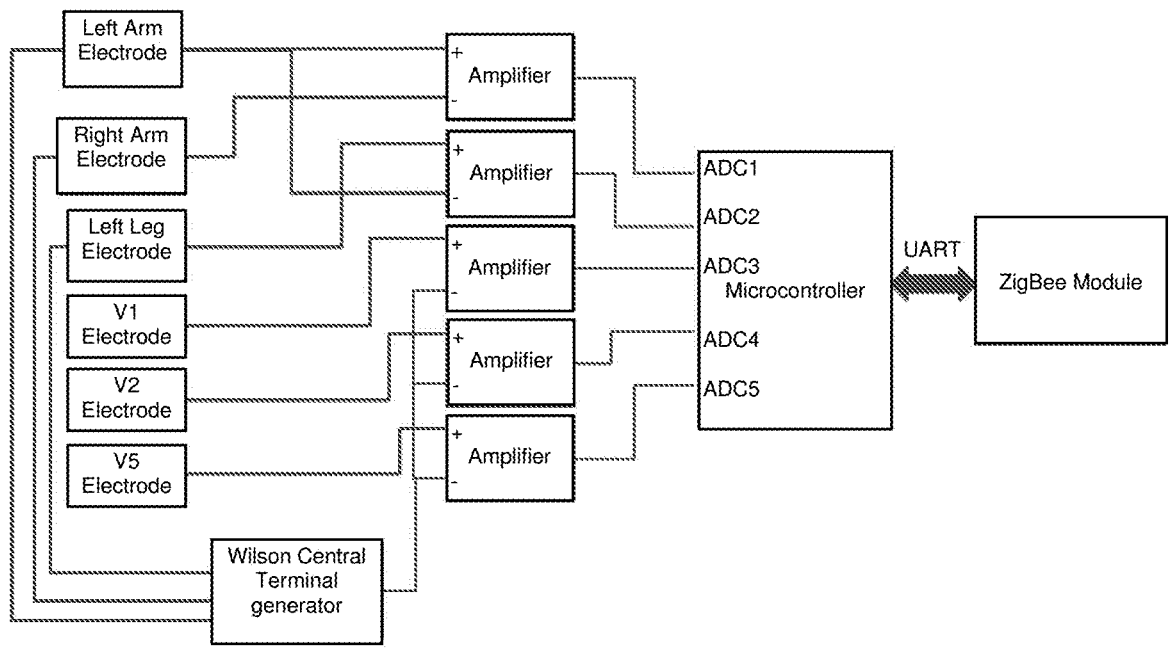
FIG. 27 shows a schematic of the wireless module.
Figure 28A:
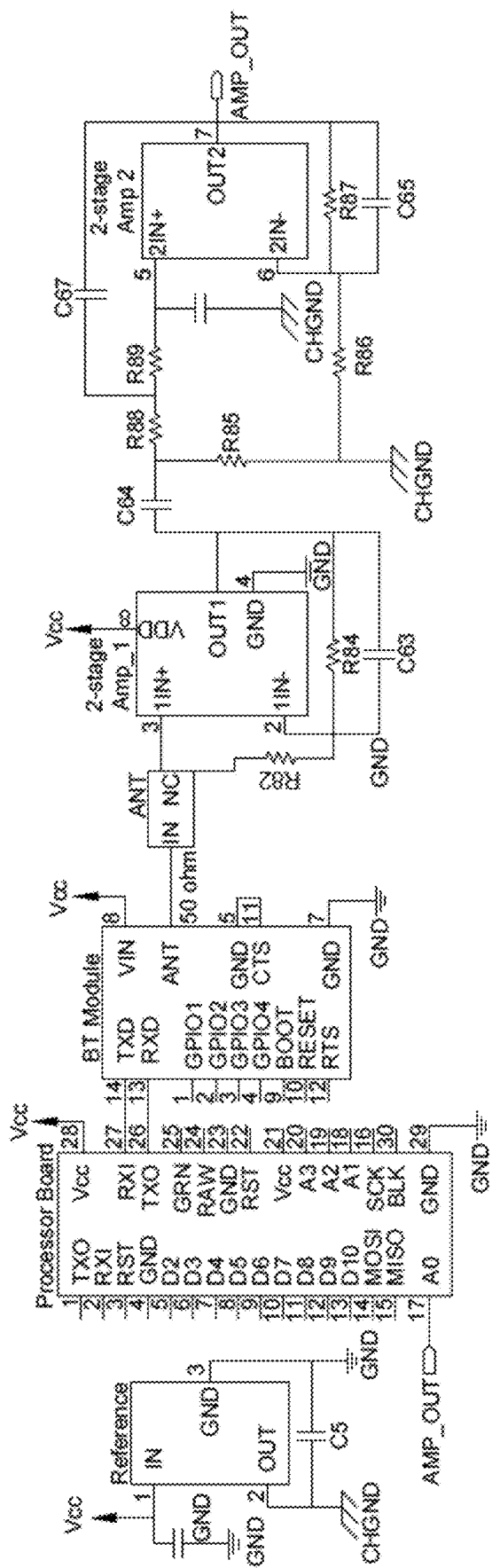
FIG. 28(a) shows a schematic of a 3-stage amplifier for use with embodiments of a wireless ECG monitoring garment system.
Figure 28B:
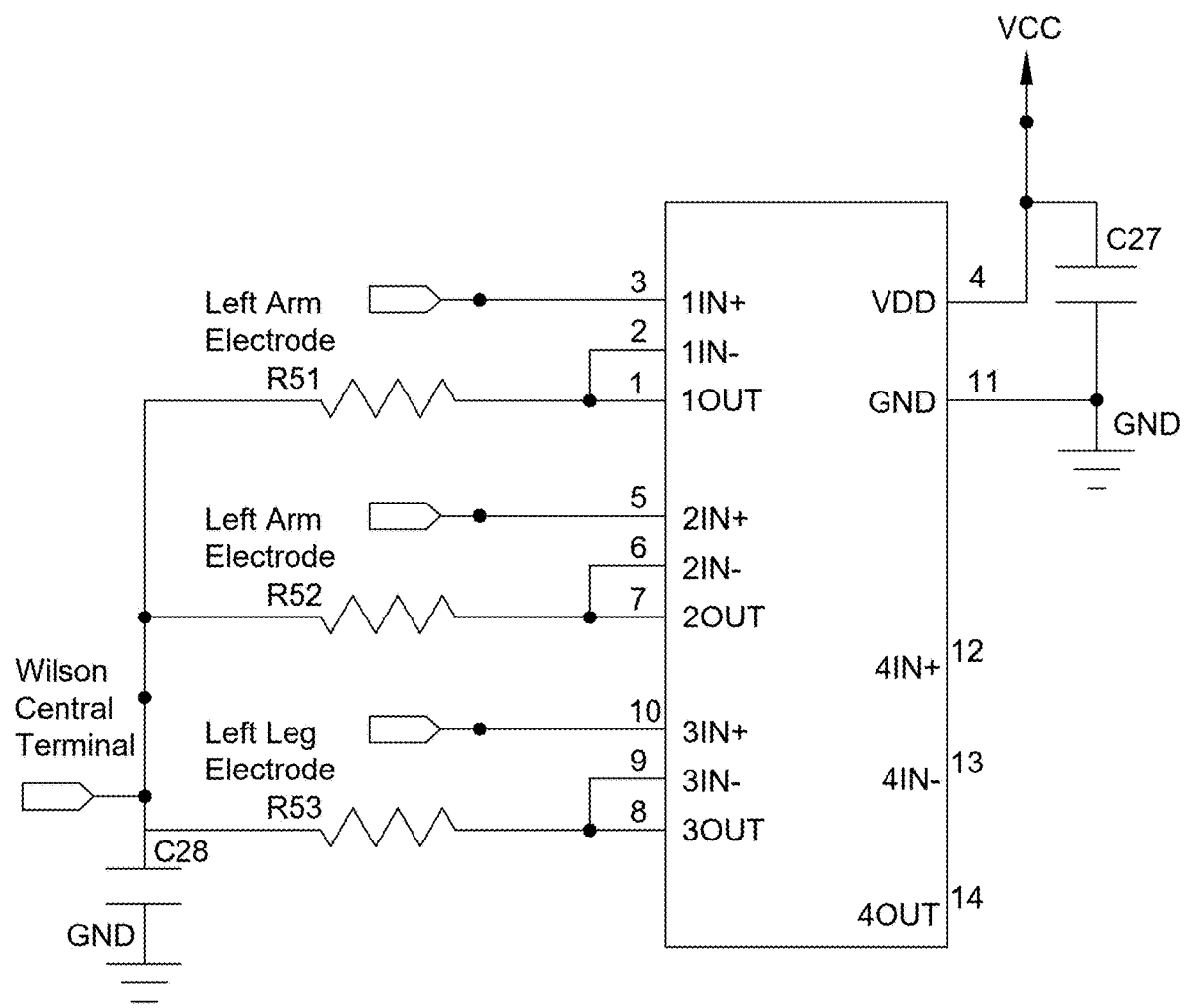
FIG. 28(b) shows a schematic of a Wilson Central Terminal (WCT) generation circuit.

The analog ECG signals acquired through the textile electrodes need to be amplified, digitized and transmitted wirelessly. The overall schematic of the wireless module is shown in FIG. 27.

Amplifier and Microcontroller

As mentioned previously, five ECG signals are acquired using the wireless module. Two are bipolar limb leads and three are unipolar precordial leads (V1, V2 and V5). The bipolar limb leads, leads I and II, are acquired between the left arm and right arm electrodes, and the right arm and left leg electrodes respectively. The average potential from the three electrodes referred to as the Wilson central terminal is generated and used as a reference for the three precordial signals. The amplifier and filter used in this system had a pass band of 0.2 Hz to 70 Hz and a gain of 50 dB. The three stage amplifier consisting of an instrumentation amplifier and two operation amplifiers, and the Wilson central terminal generation circuit schematics are shown in FIG. 20.

The amplified signals are then digitized using the onboard Analog to Digital Converter (ADC) on the ATMEL ATMEGA328P microcontroller (Atmel Corporation, San Jose, Calif.).

Wireless Module—ZigBee

The wireless module chosen for this implementation was 2.4 GHz XBee-PRO® (Digi international, Minnetonka, Minn.). This module has a range of up to 1 mile with line of sight, outdoors. Therefore, this module is more than sufficient to offer good QoS over the distance between the box office or the sideline and the football player on the field. In various embodiments, the wireless signals are encrypted to maintain privacy of the garment-wearer's data, which has added importance in cases such as competitive sports or a combat situation where knowing information about a participant's health status could give an opponent an advantage.

Software Implementation

The software to receive, plot and store the received ECG signals was developed using MATLAB (Mathworks, Natick, Mass.). In addition to the signal acquisition function, an active real-time motion artifact removal algorithm was also used to minimize the effect of motion on the baseline of the ECG signal. This algorithm is described in Kwon et al. (Proc. SPIE 7980, Nanosensors, Biosensors, and Info-Tech Sensors and Systems 2011, 79800K, incorporated herein by reference).

Results

Figure 29A:
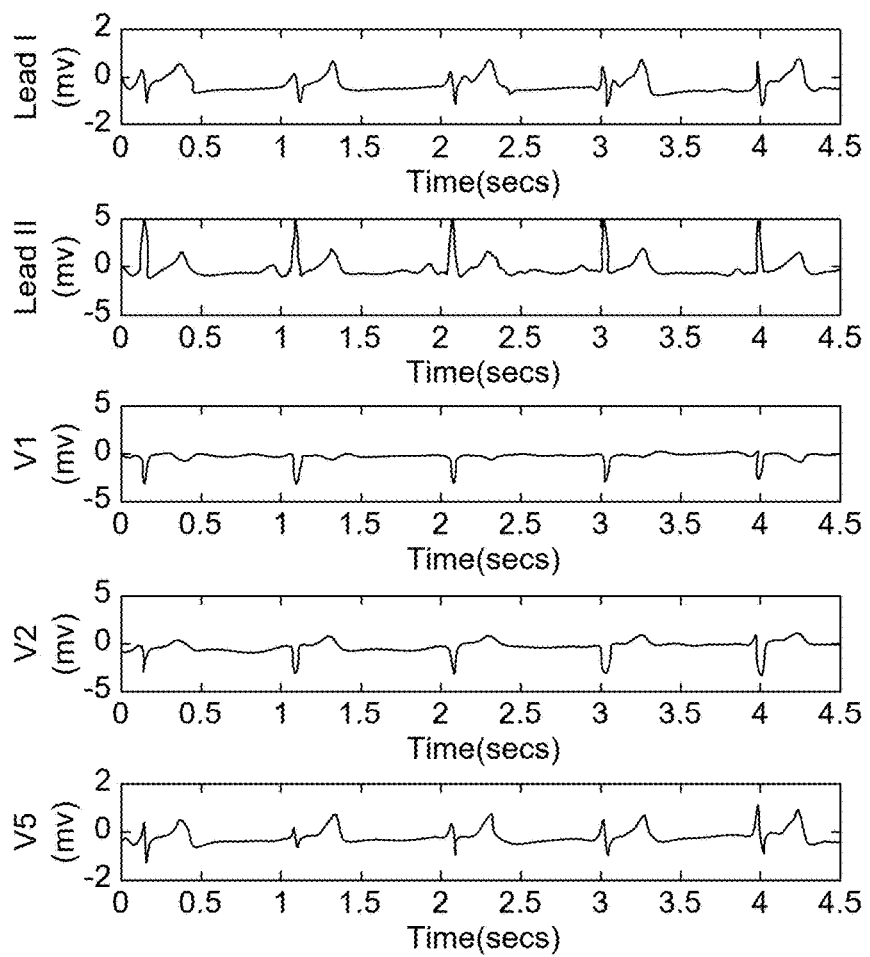
FIG. 29(a) shows ECG signals acquired using the system having Lead I and II, precordial leads V1, V2 and V5.
Figure 29B:
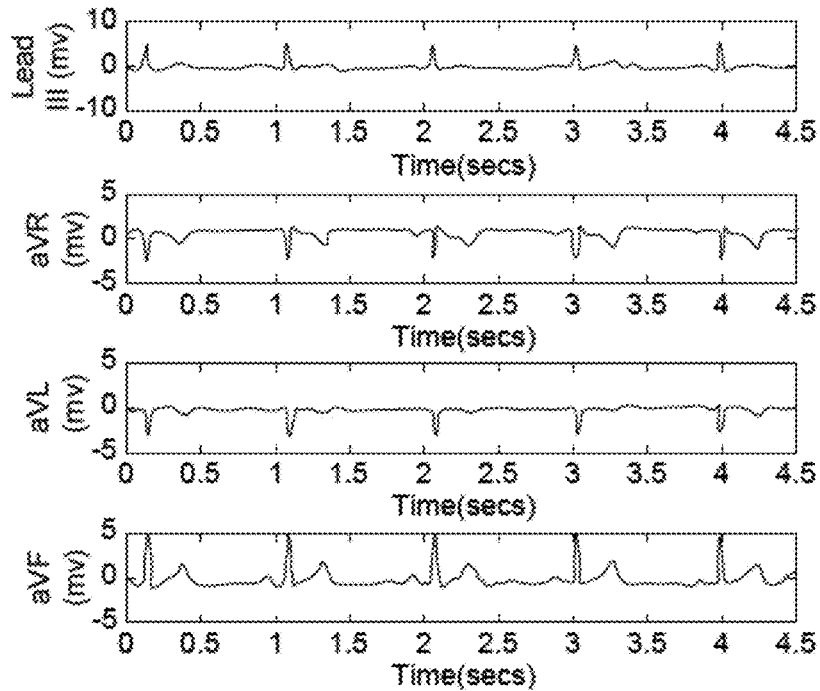
FIG. 29(b) shows Lead III and augmented limb leads derived from signals in FIG. 29(a).

The data acquired through the system for a normal 25 year old subject is plotted in FIG. 29. FIG. 29(*a*) shows the five signals, namely Leads I and II, and the three precordial signals V1, V2 and V5. FIG. 21(*b*) shows Leads III, aVR, aVL and aVF, which are derived from Lead I and Lead II. As can be observed, the acquired signals are comparable in quality to a regular clinical 12-lead ECG.

In various embodiments, ECG signals such as those shown in FIG. 29 are analyzed to identify one or more abnormality in the ECG, for example an inverted T-wave. In some embodiments, automated software routines are used to identify the abnormalities, including pattern recognition and machine-learning algorithms. In addition to identifying the presence of an abnormality, factors such as the amplitude and frequency of the abnormal pattern will determine whether the abnormality is of concern. When an abnormality is identified, for example by the controller associated with the wireless receiving station, a signal may be sent to medical personnel.

Exemplary Nanocomposite Inks for Providing Conductive Traces

Nanocomposite ink, as described above, comprises nanoparticles, nanostructures and mesostructures suspended in organic binder such as acrylic, epoxy, heat curable, and photo curable resins.

The nanoparticles, nanostructures and mesostructures have electrical conductive functional groups on their surface, providing superior electrical conductivity as compared to inks and uncoated CNTs and MWCNTs (Multi Wall Carbon Nano Tubes). These nanocomposite inks can be applied to flexible substrate(s) using screen printing, gravure printing, stamping, printing by doctor(s) blade methods.

Figure 30:
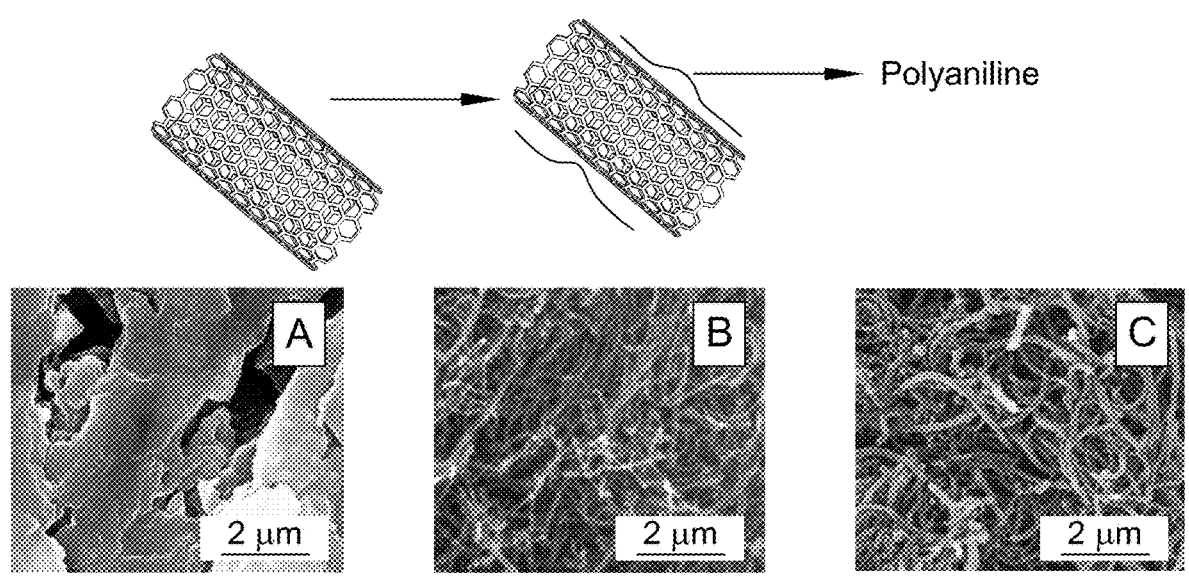
FIG. 30 shows SEM images of polyaniline (A), MWCNTs (B) and polyaniline coated MWCNTs (C).

Carbon nanotubes can be coated with conductive polymers such as polyaniline as shown in FIG. 30, which illustrates SEM images of polyaniline (A), MWCNTs (B) and polyaniline coated MWCNTs (C). While pure MWCNT have an average diameter of ~28 nm (or in the range of 12-50 nm), polyaniline coated MWCNT have an average diameter of ~41 nm (or in the range of 18-75 nm).

Variations in mix ratios (volume per volume) of polyaniline coated MWCNT against un-coated MWCNT as conductive filler(s) in acrylic binder are shown in the following table.

| Mix Ratio | MNCNT | | PA Coated MNCNT | |
|---|---|---|---|---|
| (v/v) | wt % | $R_s$(mΩ/square) | wt % pure CNT | $R_s$(mΩ/square) |
| 1:1 | 11 | 1.941 ± 0.547 | 1.4 | 1.24 ± 0.139 |
| 2:1 | 19 | 1.347 ± 0.259 | 2.8 | 0.9 ± 0.147 |
| 4:1 | 26 | 1.226 ± 0.191 | 4.1 | 0.85 ± 0.148 |
| 8:1 | 32 | 1.12 ± 0.079 | 5.5 | 0.95 ± 0.212 |

The data shows superior electrical conductivity (lower sheet resistance $R_s$) with substantially less CNT loading in case of polyaniline coated MWCNT. The mix ratio refers to the volume per volume mixture of conductive filler (MNCNT or PA Counted MNCNT) and acrylic binder. The above table shows the variation in resistance values with change in mix ratio. The electrically conductive ink made of PA coated MWCNTs should have resistance value of less than 1 mΩ/sq. The minimum mix ration required is 2 parts PA coated MWCNT and 1 part binder.

Similarly, nanocomposite inks of polyaniline coated MWCNT mixed in polyurethane or silicone can be formulated to achieve stretchable thin films. Such material can be implemented as sensor, electrical connection and electrical functional layer (in this example, poly-aniline).

The end product is a nanoparticle based ink with better electrical performance and applicability over a large substrate.

Other examples are given below:

Silver nanoparticles stabilized in ink solutions by organic ligand shells such as thiol polymers, which can also be removed after printing are shown in FIG. 31. In particular, FIG. 31 shows SEM photographs of (A) thiol functionalized polymer capped silver nanoparticle and (B) pure silver nanoparticle. The process for silver nanoparticles deposition can be done by methods such as electrolysis, sol-gel method, micro-emulsion, chemical reduction. In this regard, the thiol polymer ligand shell act as surfactants for the silver nanoparticles. Once the ink is printed on textile substrate, the surfactant properties of ligand shell are not required. Accordingly, the ligand shell can be removed by dissolution.

Figure 32:
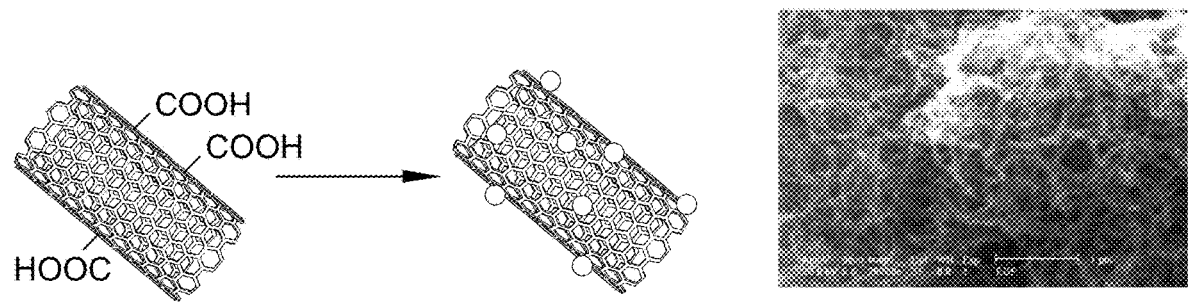
FIG. 32 shows a achematic diagram of the deposition of Ag/CNT and SEM image of the deposition of Ag/CNT.

Carbon nanotubes can be coated with conductive nanoparticles such as silver as shown in FIG. 32, which is a schematic diagram of the deposition of Ag/CNT and SEM image of the deposition of Ag/CNT. The nanoparticles may be coated with an electrically conductive polymer, forming a core and a shell with binding properties, thus making a binderless ink formulation. In this regard, the polymer coating is conductive and also serves as the binding agent. The conductive polymer coating is preferably poly-aniline. The conductivity of such a formulation will be higher than those with a separate binder because of higher fill percentage of MWCNT per unit volume of the ink.

Figure 33:
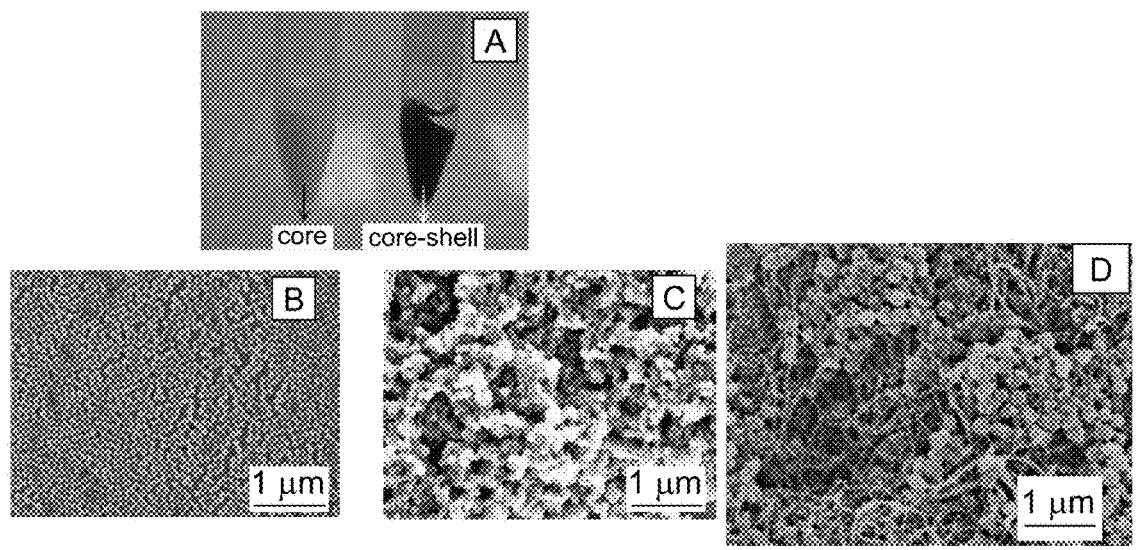
FIG. 33 shows a photo of core and core and shell particles (A) and SEM images of core particle (B) and core and shell type (C) and SEM images of functionalized CNTs/Core and shell particles based ink (D).

FIG. 33 shows core and shell with CNT that form thin film without binding agents. In particular, FIG. 33 shows photos of core and core and shell particles (A) and SEM images of core particle (B) and core and shell type (C) and SEM images of functionalized CNTs/Core and shell particles based ink (D). These inks do not require separate binders.

Printing Processes Using Nanocomposite Ink Formulations for Traces and Sensors

Figure 34:
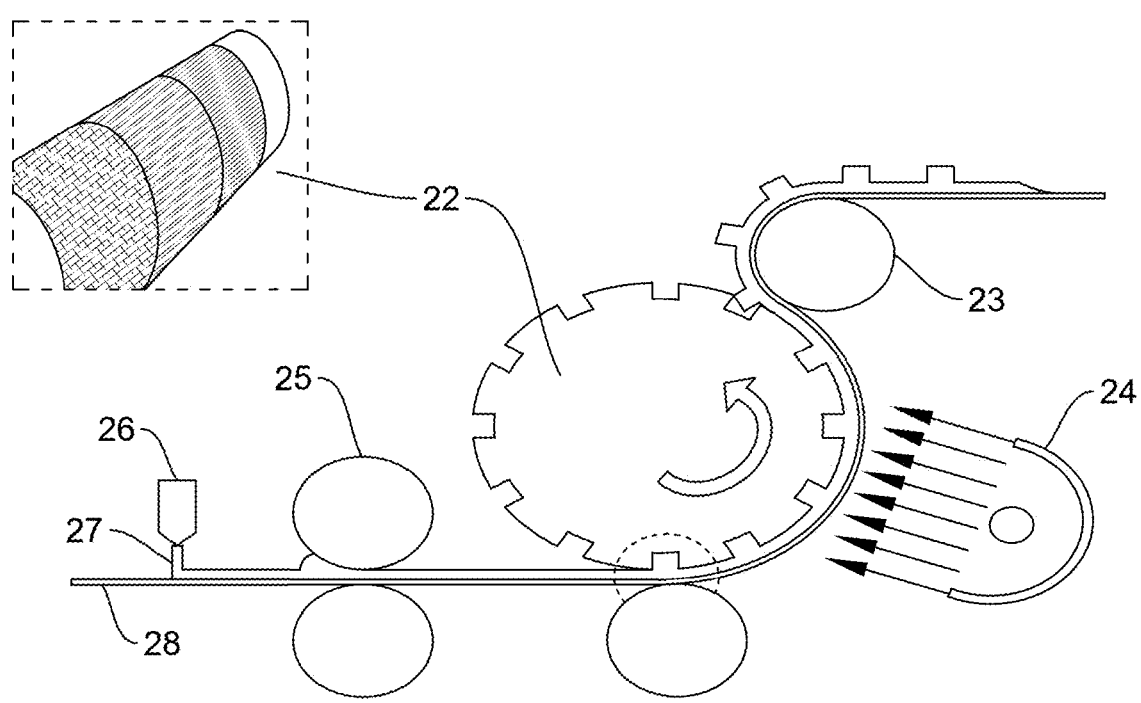
FIG. 34 illustrates a nanoprinting process.

The Nanocomposite ink formulations described above are compatible with printing processes. For example, nanoimprinting that is a unique pattern transfer technique that should not be compared with deposition techniques. The process is described in detail in FIG. 34. The negative pattern of the nanostructure is etched on the drum 22. The flexible substrate 28 is run on a set of rollers 23 and 25. The nanoparticle/mesoparticle based ink 27 is applied on the flexible substrate 28 by ink applicator 26 through a screen having a desired pattern. The pattern can include, for example, both nanosensor pads as well as conductive tracks. The locations of the nanosensor pads (and conductive tracks if desired) matches the pattern on the drum. As ink 27 (already patterned by the screen) is then imprinted on by the pattern drum 22 and ink is cured using heat source 24.

In this regard, the ink applied before roller 25 can have thickness varying from 50 microns to 100 microns. Roller 25 flattens the film out. Ink that adheres to the roller 25 can be removed with a scraper if desired.

The thickness is reduced to less than 50 microns. The thickness is such that it accommodates the height of vertically standing nanostructures and leave sufficient material to act as base. In this regard, the nanoparticles in the ink are typically no larger than about 50 nm, whereas the imprinted nanostructures formed by the drum are 200 nm or more in diameter and approximately 10-20 microns in height. Thus, a vertically standing nanostructure is formed from nanocomposite material randomly aligned with the nanostructure.

The unnumbered roller is used to apply pressure against the drum 22. This applied pressure helps drum 22 to press on to the conductive ink coated substrate to make the nanoimprint.

The heat source 24 can be a convection heater or a radiating heater type. The curing temperature is selected based on the type of binder being used in the ink. As the ink is made of nanoparticles and binder suspended in solvent, the aim of the curing process is to dry the the conductive ink coated substrate such that any traces of solvent are removed.

The etching for making the negative pattern on the drum is performed by a separate prior process using, for example, optical etching tools such as laser, 2-photon or e-beam lithography. The etched pattern can be on the drum itself, or on a sheet or plate mounted to the drum as is known in the art.

The conductive ink is used as a bulk material. After going through the nanoimprint drum 22, the bulk material is molded to form vertically standing nanostructures made of the nanocomposite ink. The surface of the molded conductive ink is used as nanosensor surface.

Although the nanocomposite ink formulations are discussed above in connection with providing conductive tracks, these nanocomposite ink formulations can also be used as a medium for connecting nanosensors and contact pads of the conductive tracks. The connection between sensor and conductive tracks, and conductive tracks and external circuitry can be done by using cold soldering options such as dispensing nanocomposite ink using precision dispensing gun.

Scalability

The functional group(s) covered nanoparticle based ink is applicable over a large flexible and rigid substrate for making nanosensors, conductive tracks and connectors. Each smallest manufactured unit of nanosensors, conductive tracks and connectors can be scaled by using the connectors to form active matrices or daisy chained circuits to obtain nanosensor arrays. In this regard, the nanosensor and conductive tracks electronics is scalable. The printed nanosensors and conductive tacks can cover large textile substrates by forming a network of nanosensors connected in the aforementioned ways. Such nanosensor systems can be integrated into bedsheets and pillow cases.

Thus, the invention provides, among other things, a wearable remote monitoring system. Various features and advantages of the invention are set forth in the following claims. It will be apparent to those skilled in the art that various modifications and variations can be made to the smart materials, dry textile sensors, and electronics integration in clothing, bed sheets, and pillow cases of the present disclosure without departing from the scope of the invention. Throughout the disclosure, use of the terms "a," "an," and "the" may include one or more of the elements to which they refer. Other embodiments of the invention will be apparent to those skilled in the art from consideration of the specification and practice of the invention disclosed herein. It is intended that the specification and examples be considered as exemplary only.

What is claimed is:

1. A wearable remote electrophysiological monitoring system, comprising:
 a garment having at least one dry contact sensor, the dry contact sensor including at least one nanostructured, textile-integrated electrode attached thereto, the nanostructured, textile-integrated electrode including a piece of fabric having between 10,000 and 100,000 nanostructures per square centimeter of fabric, the fabric including electrically conductive fibers, said nanostructures having vertically standing nanowires, the vertically standing nanowires projecting from the fibers to varying lengths of between 0.01 and 10 micrometers, the nano vires arranged to make contact with the wearer's skin, wherein the vertically standing nanowires are vertically standing when viewed relative to the fabric when the fabric is in a horizontal plane, wherein the conductive fibers include textile fibers blended or coated with metal, wherein the vertically standing nano vires are comprised of polymer nanofibers coated with a conductive material;
 a control module in electrical communication with the at least one nanostructured, textile-integrated electrode; and
 a remote computing system in communication with the control module.

2. The wearable remote electrophysiological monitoring system of claim 1, wherein the dry contact sensor is electrically connected to the control module by a conductive thread, the conductive thread comprising a conductive fiber core and an insulation sheath, the conductive fiber core including nanofibers or mesofibers made of a metal or a graphine structure.

3. The wearable remote electrophysiological monitoring system of claim 1, wherein the polymer nanofibers are made of a material selected from the group consisting of polyethylene terephthalate, polyethylene naphthalate, polybutylene terephthalate, polyester, polyurethane, polystyrene, polyvinyl alcohol, ethylene vinyl alcohol, polyacrylamide or poly lactic acid.

4. The wearable remote electrophysiological monitoring system of claim 1, wherein the conductive material is selected from the group consisting of silver, gold, platinum, polyaniline, polypyrrole, poly(3,4-ethylenedioxythiophene), titanium oxide, iron oxide, and zinc oxide.

5. The wearable remote electrophysiological monitoring system of claim 4, wherein the conductive material is polyaniline.

6. The wearable remote electrophysiological monitoring system of claim 1, wherein the nanostructures are formed by nano-imprinting by applying a nanocomposite ink to a fabric in a pattern, and forming vertically standing nanowires from the nanocomposite ink molded with an etched drum.

7. The wearable remote electrophysiological monitoring system of claim 1, wherein the dry contact sensor is electrically connected to the control module by silver-coated thread.

8. The wearable remote electrophysiological monitoring system of claim 1, wherein the at least one nanostructured textile electrode includes a plurality of nanostructured textile electrodes interconnected by printed conductive tracks comprising a flexible nanocomposite trace wherein the flexible nanocomposite trace includes silver nanoparticles and an elastic acrylic based binder.

9. The wearable remote electrophysiological monitoring system of claim 1, wherein at least one of the nanostructures comprises a one-dimensional nanostructure.

10. The wearable remote electrophysiological monitoring system of claim 9, wherein the one-dimensional nanostructure comprises a wire or a tube.

11. The wearable remote electrophysiological monitoring system of claim 1, wherein at least one of the nanostructures comprises a bump.

12. The wearable remote electrophysiological monitoring system of claim 1, wherein at least one of the nanostructures comprises a three-dimensional nanostructure.

13. The wearable remote electrophysiological monitoring system of claim 12, wherein the three-dimensional nanostructure comprises a helical nanostructure.

14. The wearable remote electrophysiological monitoring system of claim 1, wherein the remote computing system communicates with the control module using radio-frequency communications.

15. The wearable remote electrophysiological monitoring system of claim 1, wherein the dry contact sensor is electrically connected to the control module by a conductive trace formed from nanocomposite ink, the nanocomposite ink comprises carbon nanotubes coated with a conductive polymer.

16. The wearable remote electrophysiological monitoring system of claim 15, wherein the nanocomposite ink has a resistance value of less than 1 mΩ/sq.

17. The wearable remote electrophysiological monitoring system of claim 15, wherein the carbon nanotubes are coated with conductive nanoparticles.

18. The wearable remote electrophysiological monitoring system of claim 17, wherein the conductive nanoparticles are silver nanoparticles and the conductive polymer is polyaniline.

19. The wearable remote electrophysiological monitoring system of claim 15, wherein the conductive polymer coated carbon nanotubes are suspended in an organic binder.

20. The wearable remote electrophysiological monitoring system of claim 1, wherein the vertically standing nanowires are vertically standing conductive fibers deposited on the fabric via flocking.

21. The wearable remote electrophysiological monitoring system of claim 1, wherein the fabric has been leveled to a roughness below 100 nm by successively coating and curing the fabric with polymers having different viscosities.

22. The wearable remote electrophysiological monitoring system of claim 1, wherein the polymer nanofibers are made of a polyethylene terephthalate modified with sulfonated isocyanate.

23. A wearable remote electrophysiological monitoring system comprising:
a garment having at least one dry contact sensor, the dry contact sensor including at least one nanostructured, textile-integrated electrode attached thereto, the nanostructured, textile-integrated electrode including a piece of fabric having between 10,000 and 100,000 nanostructures per square centimeter of fabric, the fabric including electrically conductive fibers, said nanostructures having vertically standing nanowires, each of the nanostructures projects from the fibers to varying lengths of less than one micrometer, the nanowires arranged to make contact with the wearer's skin, wherein the vertically standing nanowires are vertically standing when viewed relative to the fabric when the fabric is in a horizontal plane, wherein the conductive fibers include textile fibers blended or coated with metal, wherein the vertically standing nanowires are comprised of polymer nanofibers coated with a conductive material;
a control module in electrical communication with the at least one nanostructured, textile-integrated electrode; and
a remote computing system in communication with the control module.

* * * * *